(12) United States Patent
Tacca et al.

(10) Patent No.: US 12,127,947 B2
(45) Date of Patent: Oct. 29, 2024

(54) LAMINA PLATE ASSEMBLY

(71) Applicant: GLOBUS MEDICAL, INC., Audubon, PA (US)

(72) Inventors: Nick Tacca, West Chester, PA (US); Jason Cianfrani, Conshohocken, PA (US)

(73) Assignee: Globus Medical Inc., Audubon, PA (US)

(*) Notice: Subject to any disclaimer, the term of this patent is extended or adjusted under 35 U.S.C. 154(b) by 579 days.

(21) Appl. No.: 17/402,814

(22) Filed: Aug. 16, 2021

(65) Prior Publication Data

US 2022/0031465 A1 Feb. 3, 2022

Related U.S. Application Data

(63) Continuation of application No. 15/059,366, filed on Mar. 3, 2016, now Pat. No. 11,090,166.

(51) Int. Cl.
*A61F 2/44* (2006.01)
*A61B 17/70* (2006.01)
*A61B 17/80* (2006.01)

(52) U.S. Cl.
CPC ............ *A61F 2/44* (2013.01); *A61B 17/7049* (2013.01); *A61B 17/7053* (2013.01); *A61B 17/7071* (2013.01); *A61B 17/8023* (2013.01); *A61B 17/7023* (2013.01)

(58) Field of Classification Search
CPC ............ A61B 17/7068; A61B 17/8023; A61B 17/7049
See application file for complete search history.

(56) References Cited

U.S. PATENT DOCUMENTS

| | | | |
|---|---|---|---|
| 6,066,175 A | 5/2000 | Henderson | |
| 6,080,157 A | 6/2000 | Cathro | |
| 6,235,059 B1 | 5/2001 | Benezech | |
| 6,572,619 B2 | 6/2003 | Santilli | |
| 6,576,017 B2 | 6/2003 | Foley et al. | |
| 6,635,087 B2 | 10/2003 | Angelucci | |
| 6,660,007 B2 | 12/2003 | Khanna | |
| 7,112,222 B2 | 9/2006 | Fraser et al. | |
| 7,182,782 B2 | 2/2007 | Kirschman | |
| 7,264,620 B2 | 9/2007 | Taylor | |
| 9,055,982 B2 * | 6/2015 | Chind | A61B 17/7071 |
| 9,138,325 B2 | 9/2015 | Mouw | |
| 2002/0120335 A1 | 8/2002 | Angelucci | |
| 2004/0030388 A1 | 2/2004 | Null | |
| 2005/0209694 A1 | 9/2005 | Loeb | |

(Continued)

FOREIGN PATENT DOCUMENTS

| | | |
|---|---|---|
| EP | 3213705 A1 | 9/2017 |
| JP | 2014-505522 A | 3/2014 |

(Continued)

*Primary Examiner* — Andrew Yang

(57) ABSTRACT

Lamina plate assemblies, systems, and methods thereof. A lamina plate assembly may be configured to provide lamina support following laminectomy, for example, in cervical and lumbar cases. The lamina plate assembly may include a generally elongate body having a first free end, a second free end, and a posterior portion disposed between the first free end and the second free end. Different embodiments of securing portions are used to secure the lamina plate assembly to a vertebra.

18 Claims, 28 Drawing Sheets

(56) References Cited

U.S. PATENT DOCUMENTS

| | | |
|---|---|---|
| 2005/0250379 A1 | 11/2005 | Coffey |
| 2005/0251138 A1 | 11/2005 | Boris |
| 2009/0210009 A1 | 8/2009 | Chao et al. |
| 2009/0210012 A1 | 8/2009 | Null et al. |
| 2009/0318968 A1* | 12/2009 | Duggal .............. A61B 17/8869 606/279 |
| 2010/0161056 A1 | 6/2010 | Voellmicke et al. |
| 2010/0174315 A1 | 7/2010 | Scodary et al. |
| 2010/0249842 A1 | 9/2010 | Mir |
| 2011/0106083 A1 | 5/2011 | Voellmicke |
| 2011/0106087 A1 | 5/2011 | Gamache |
| 2011/0106169 A1 | 5/2011 | Zalenski et al. |
| 2011/0125269 A1 | 5/2011 | Moskowitz et al. |
| 2012/0158060 A1 | 6/2012 | Abrahams et al. |
| 2013/0060283 A1 | 3/2013 | Suh et al. |
| 2014/0018920 A1 | 1/2014 | Mouw |
| 2015/0320447 A1 | 11/2015 | Mouw |

FOREIGN PATENT DOCUMENTS

| | | | |
|---|---|---|---|
| JP | 2014529472 A | 11/2014 | |
| JP | 2017205485 A | 11/2017 | |

\* cited by examiner

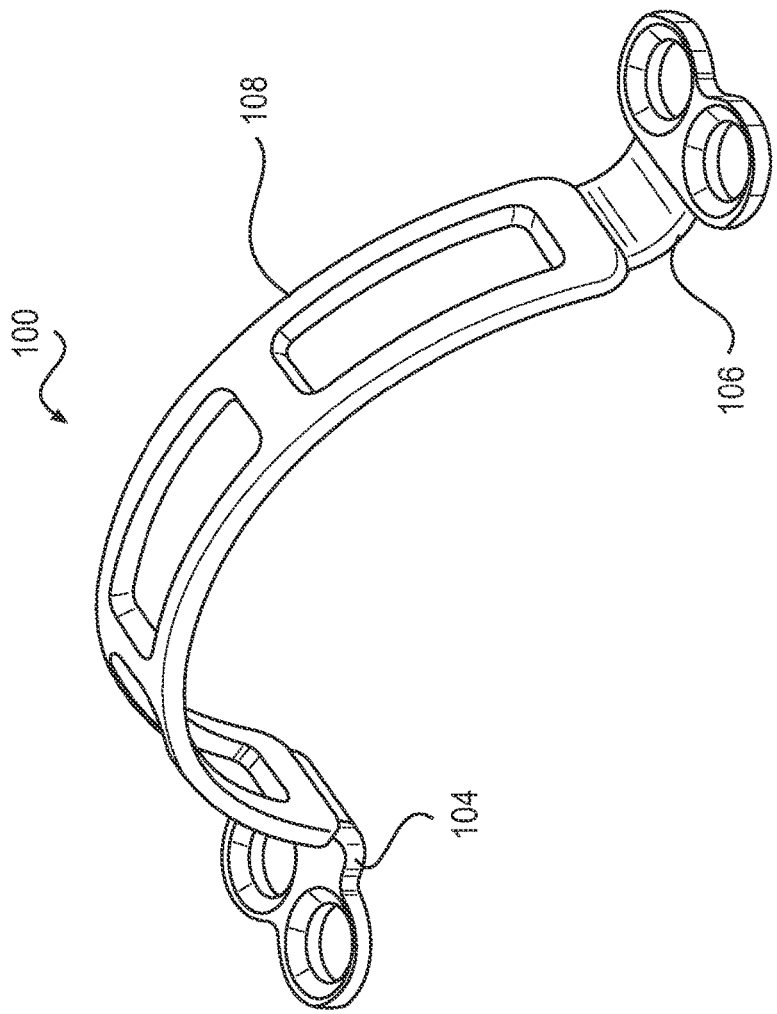
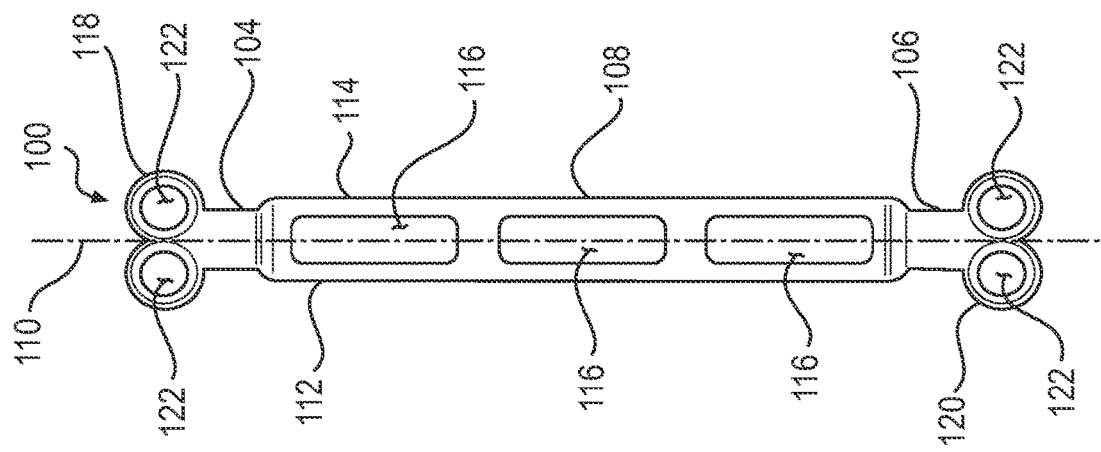

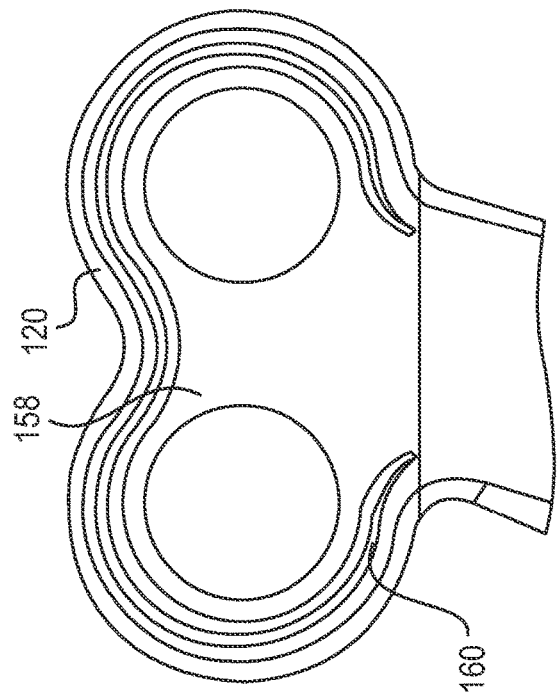
FIG. 12
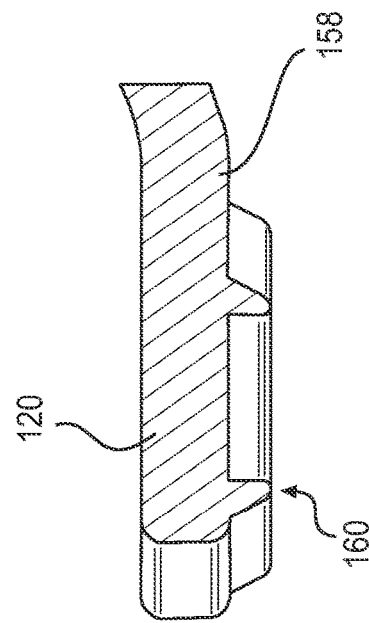
FIG. 12A
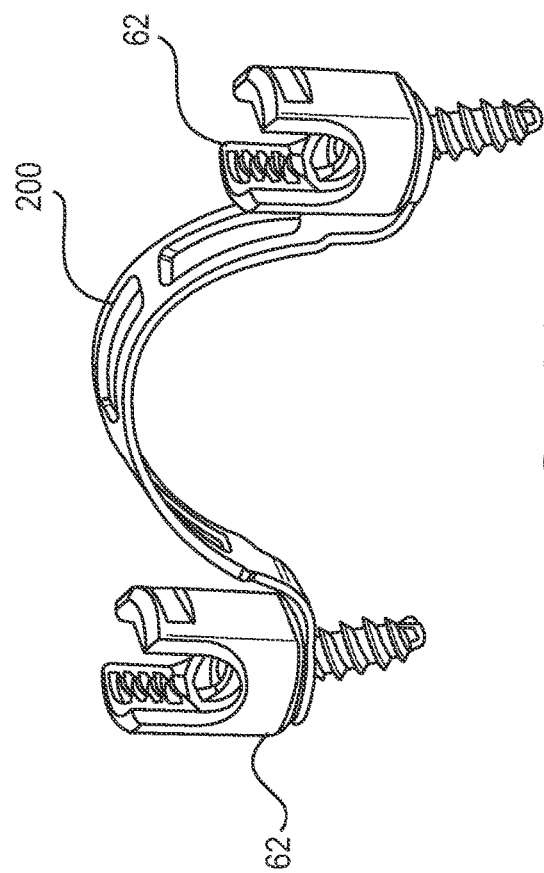
FIG. 10
FIG. 11

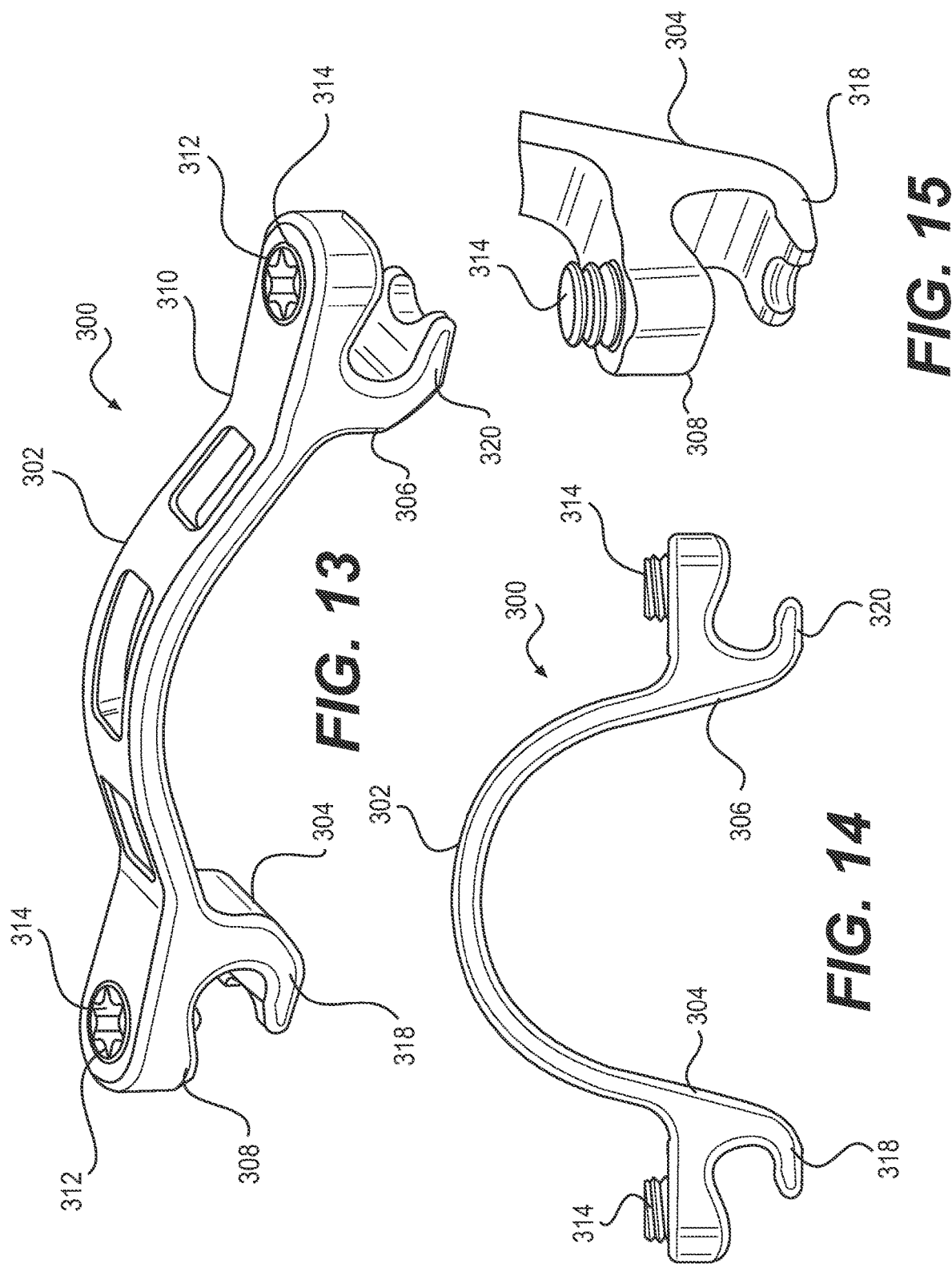

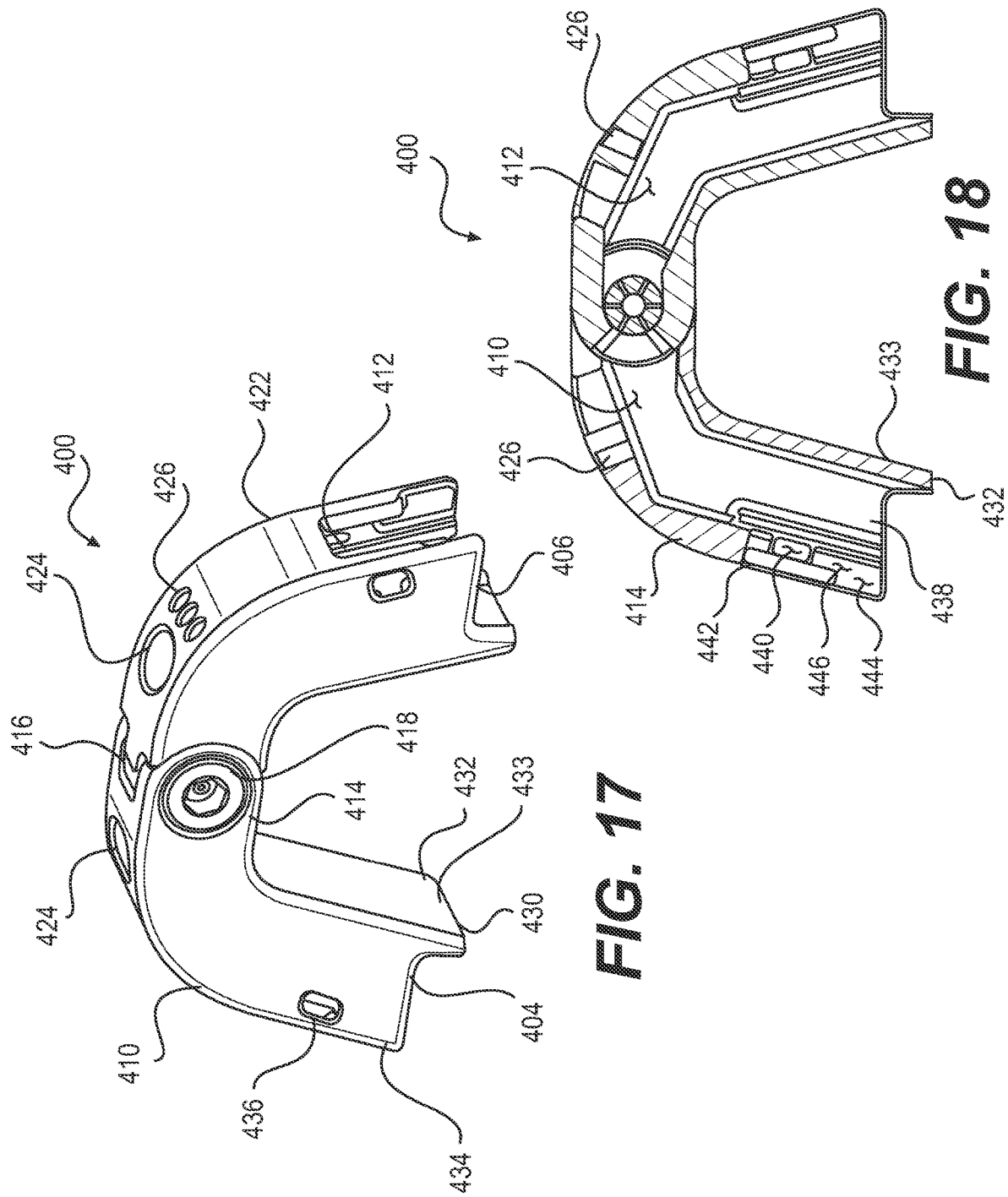

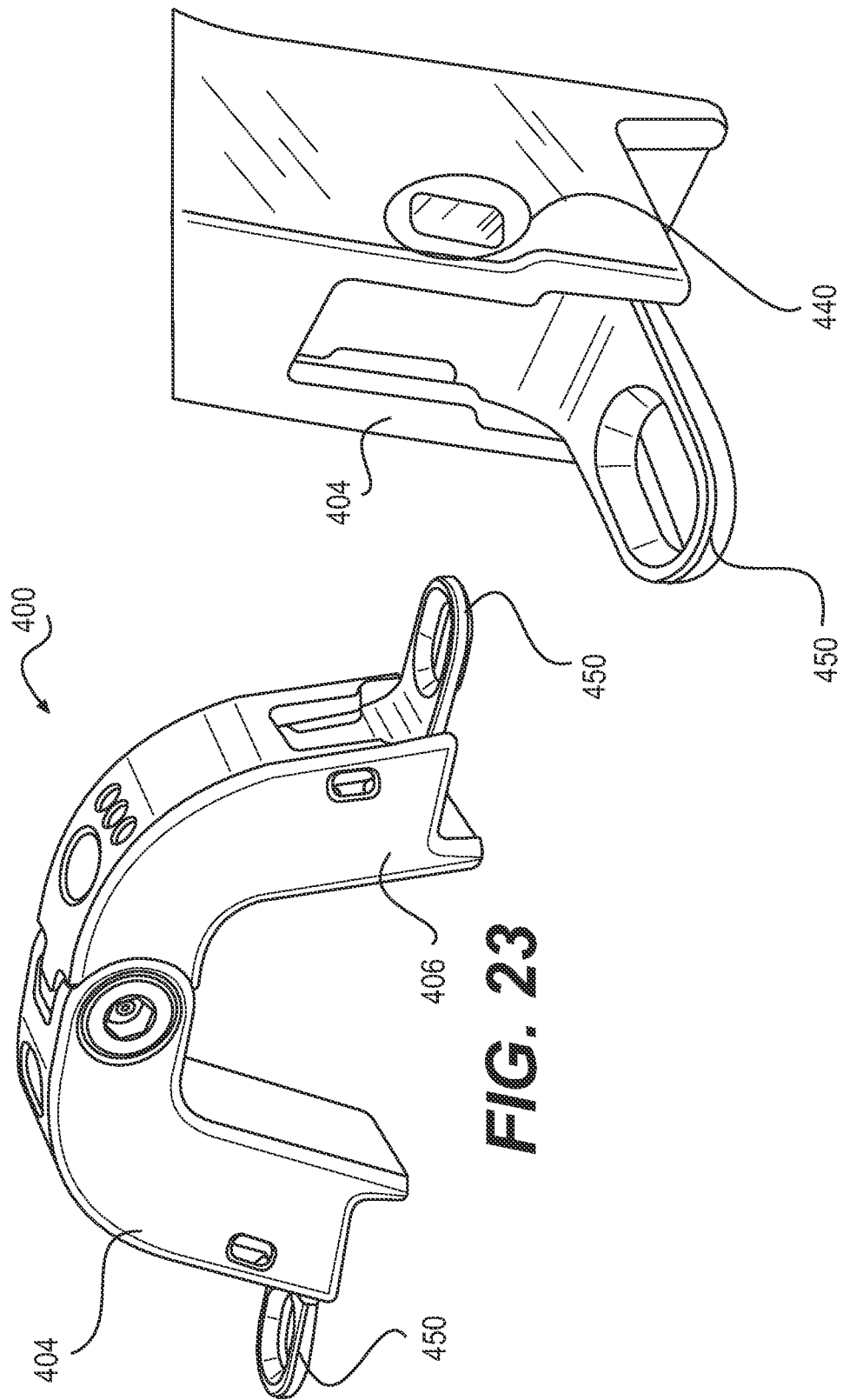

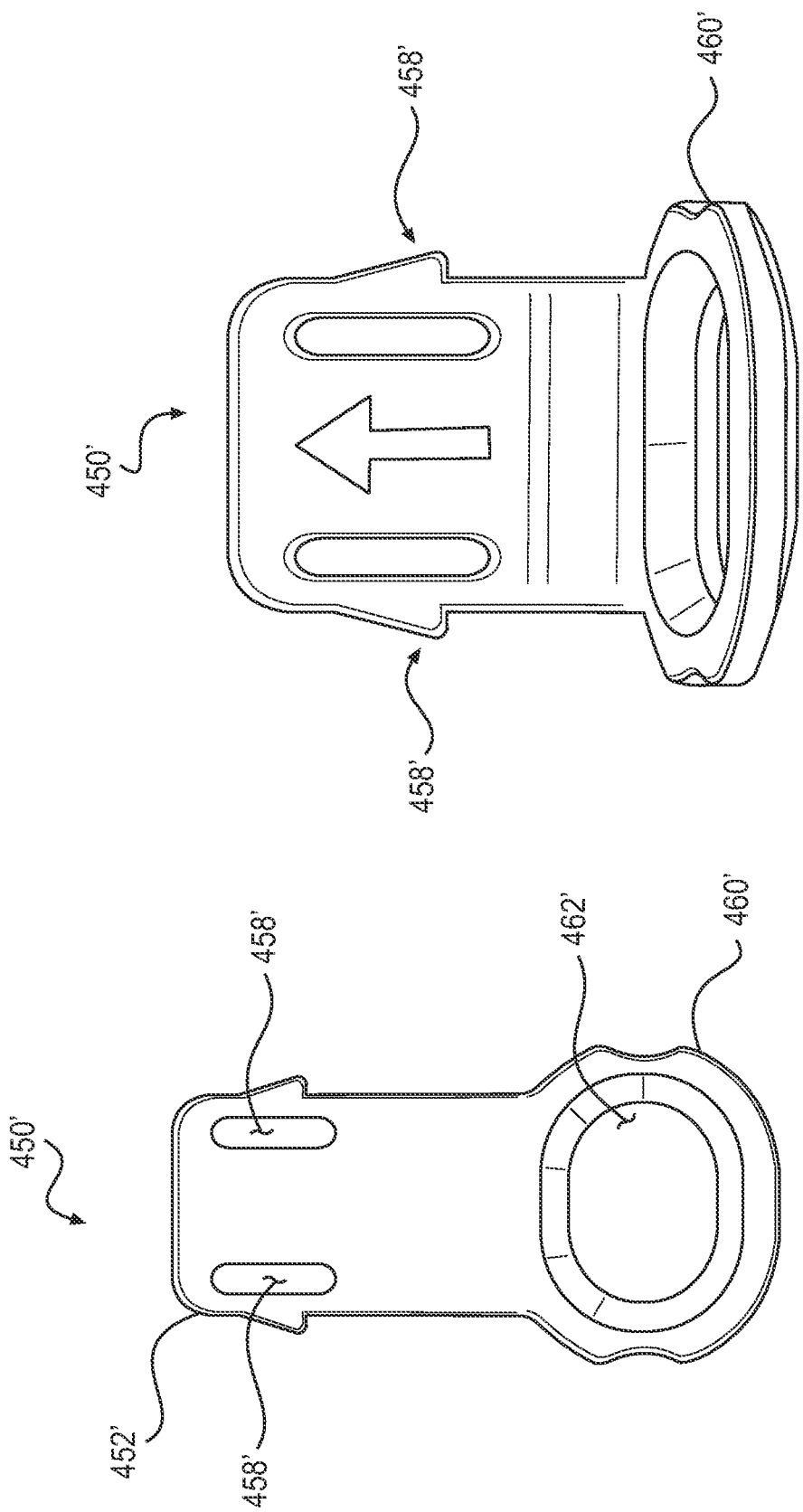

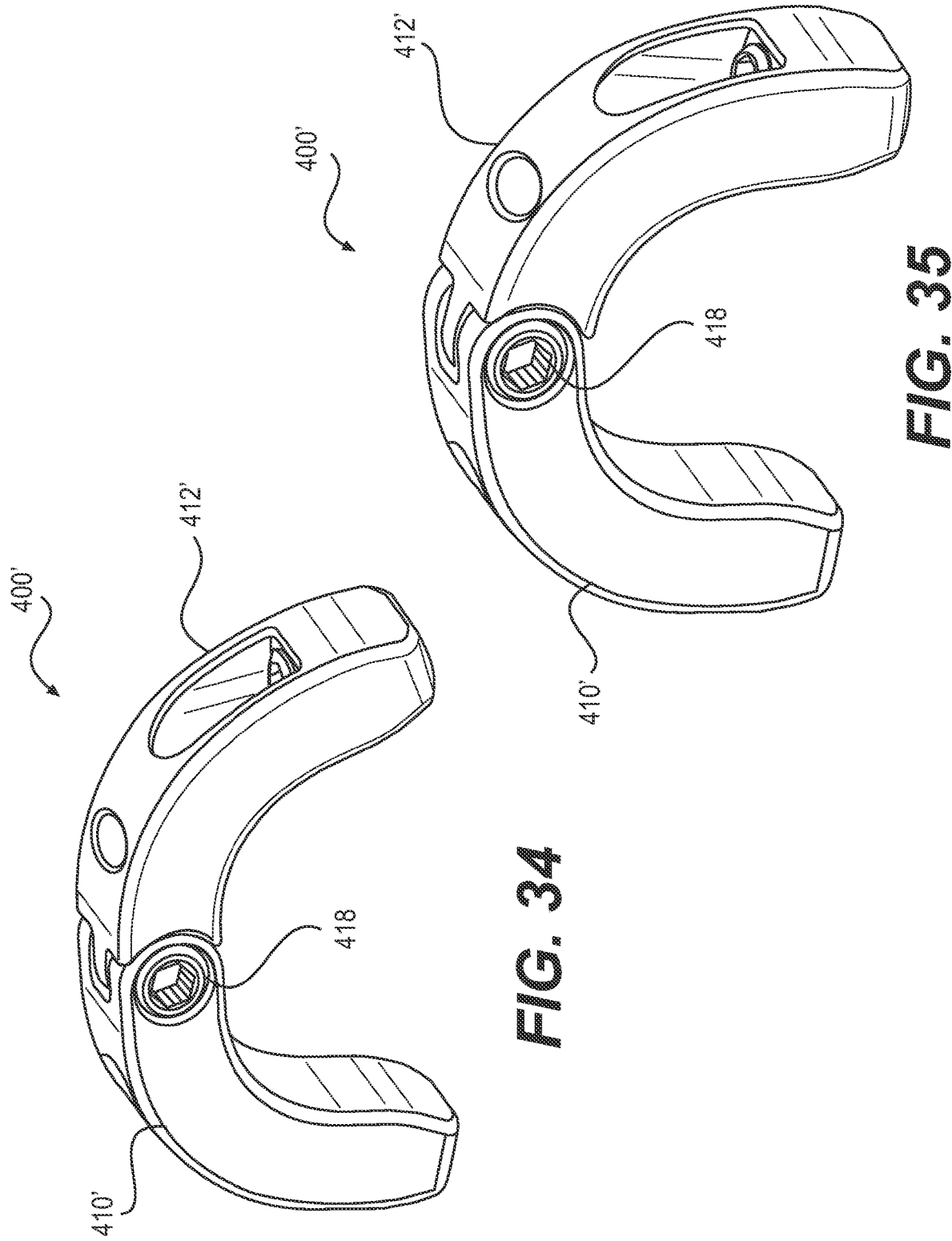

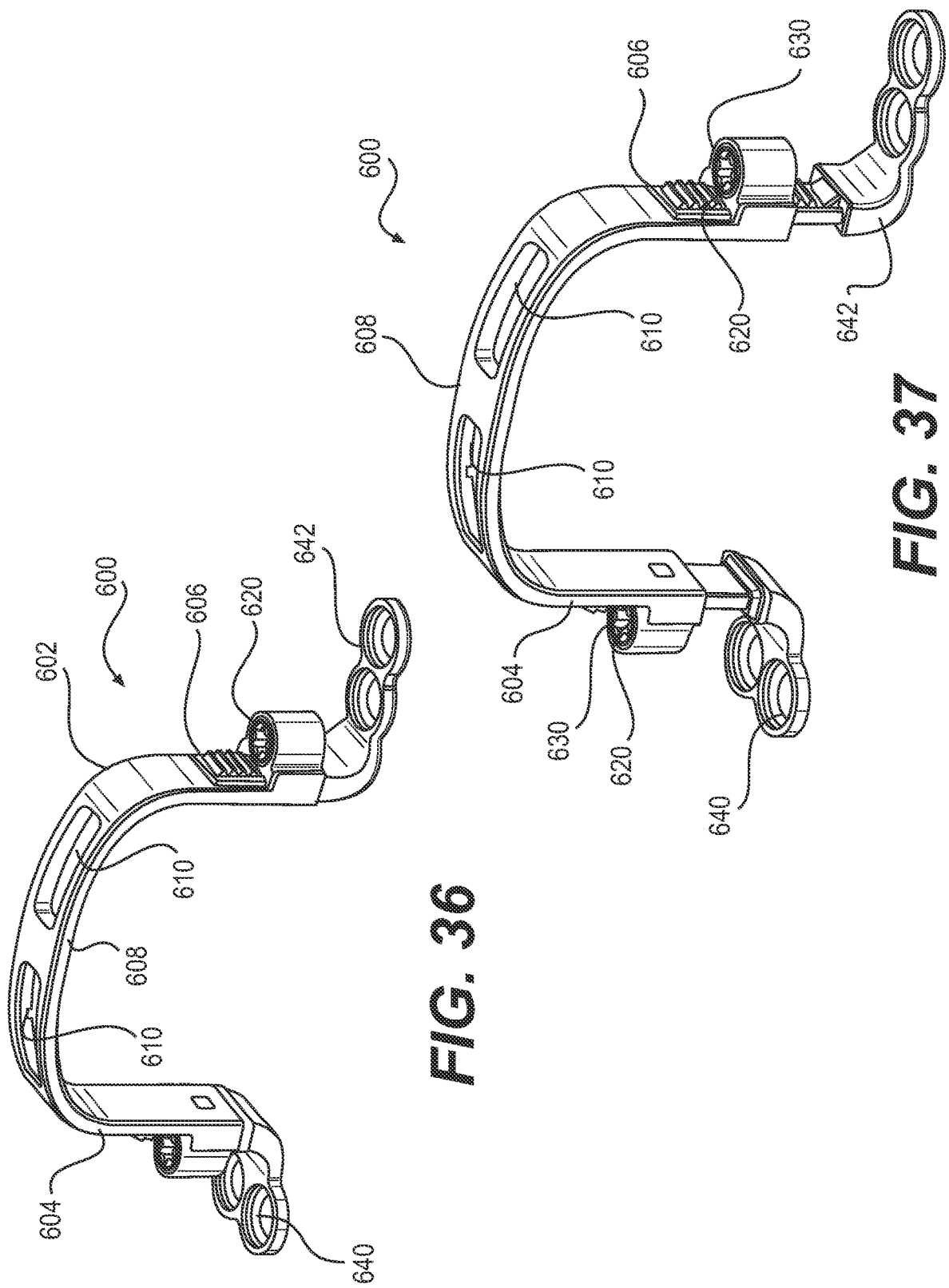

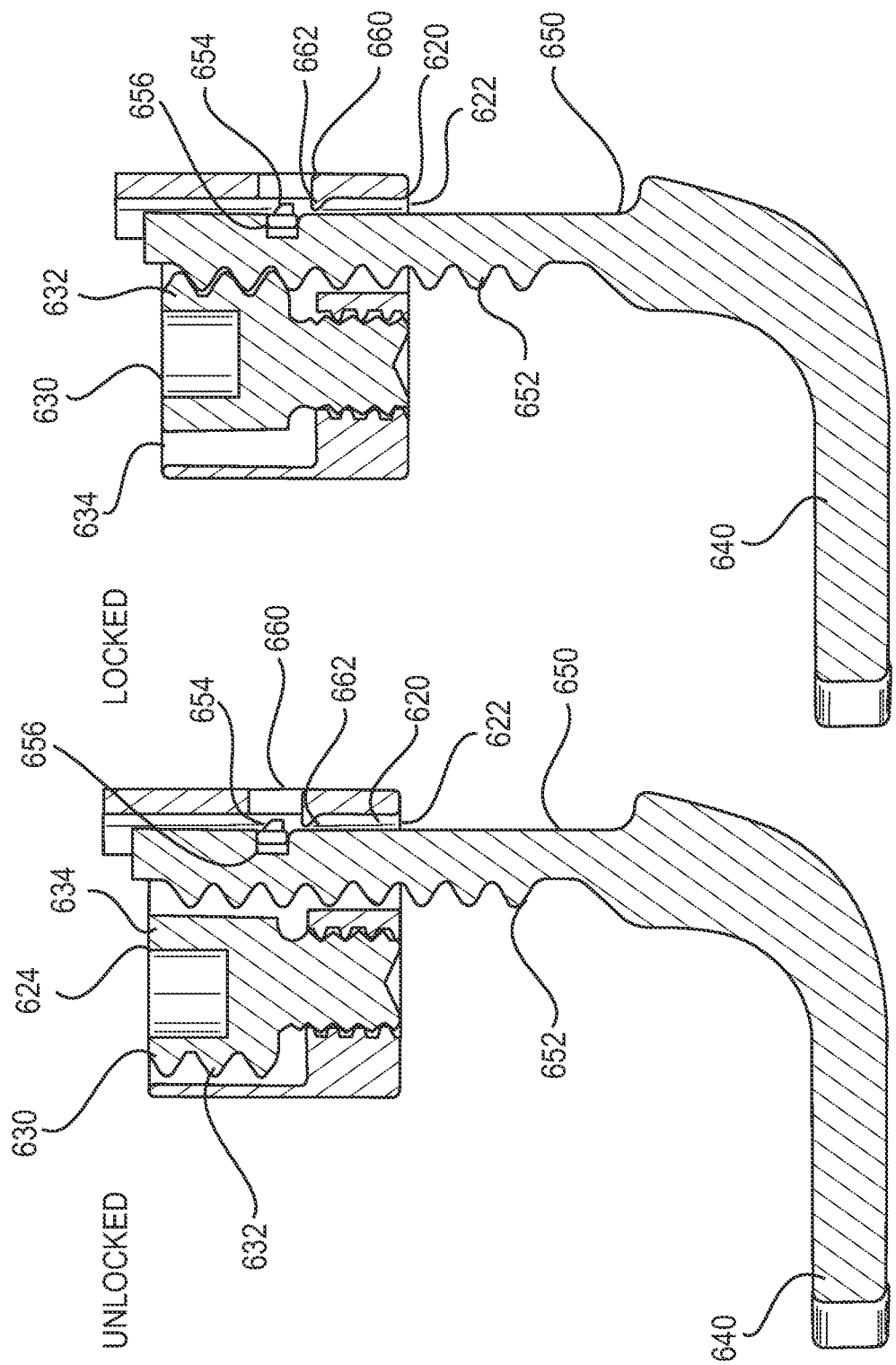

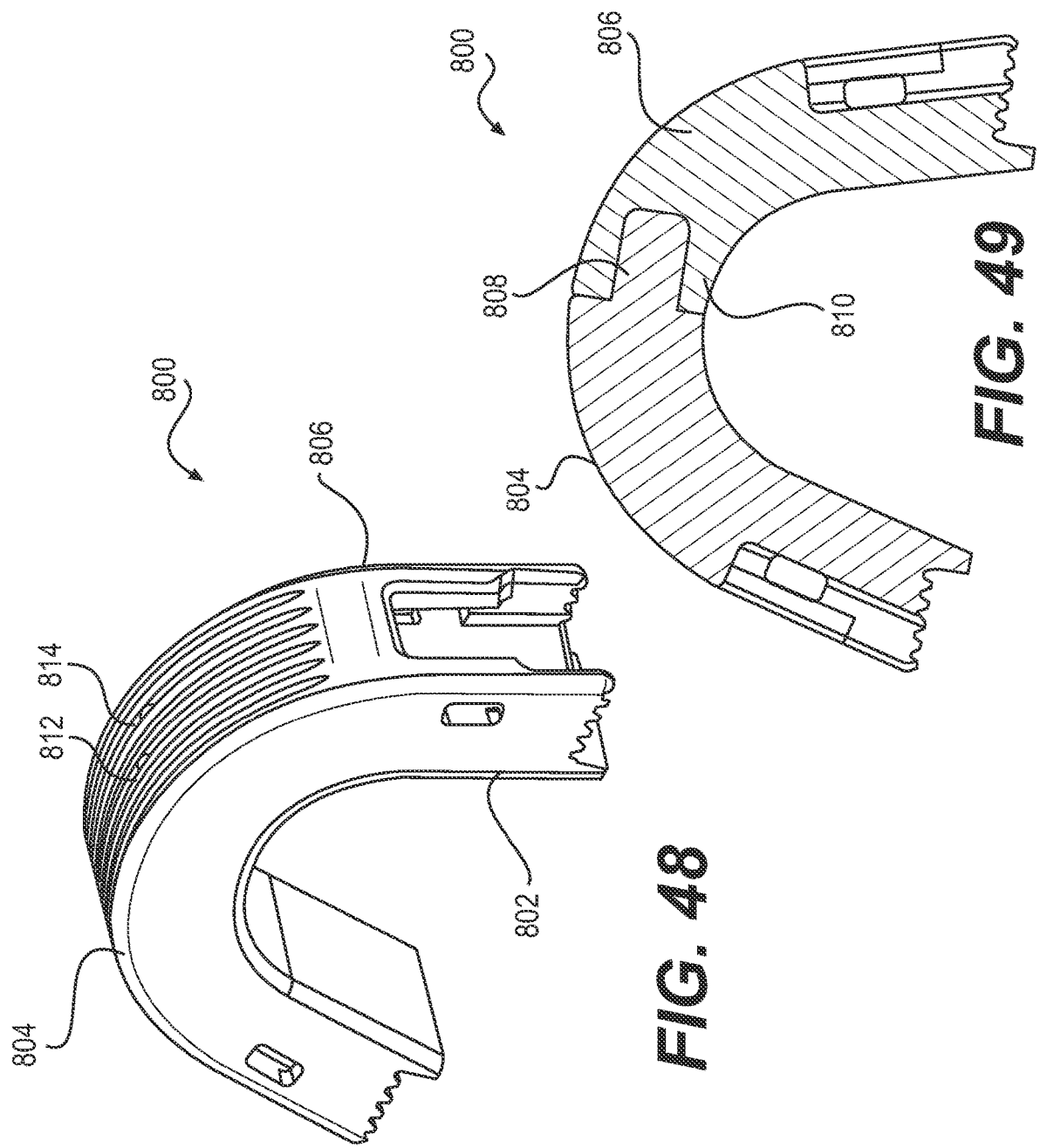

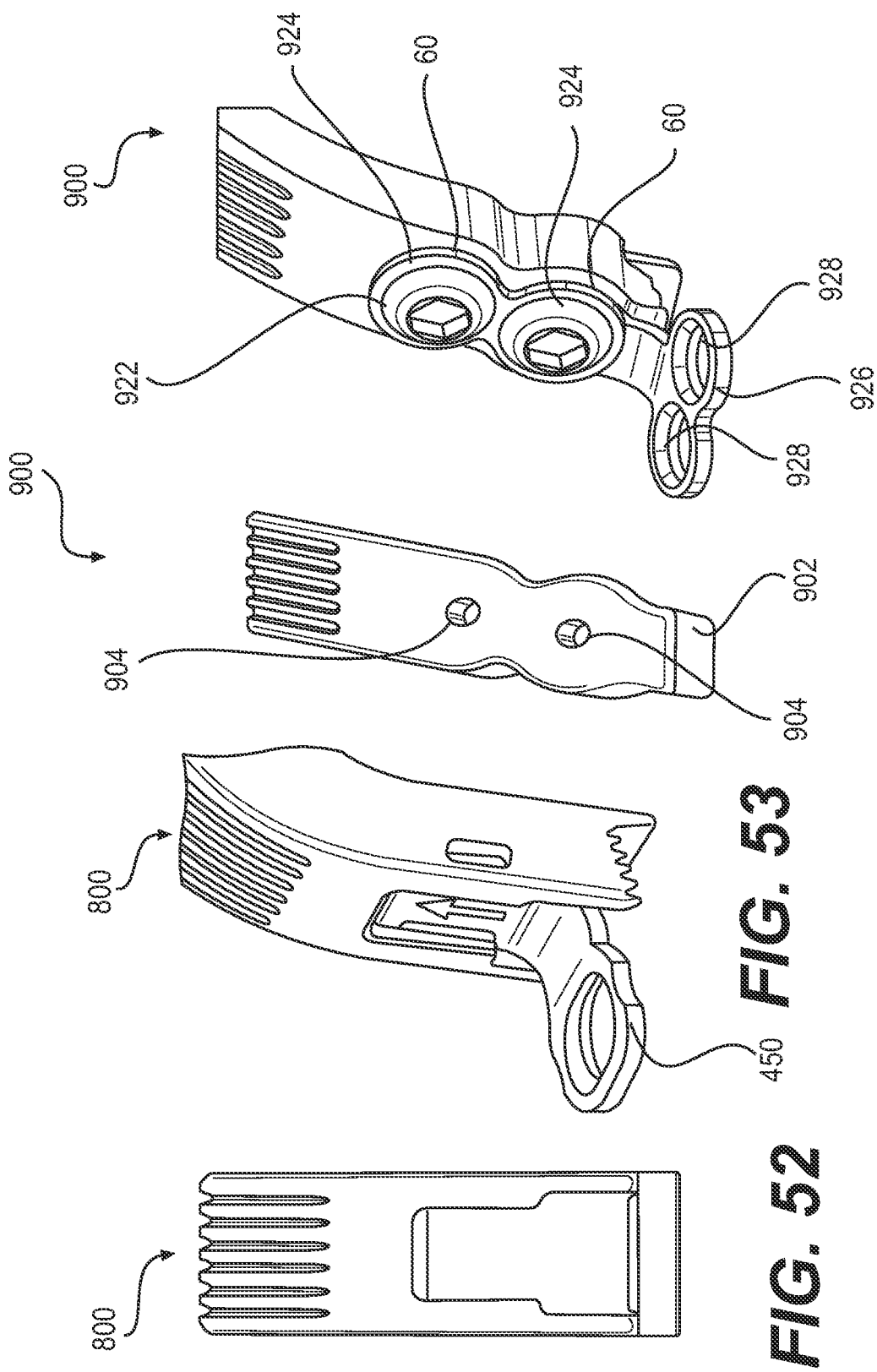

LAMINA PLATE ASSEMBLY

CROSS-REFERENCE TO RELATED APPLICATIONS

This application is a continuation of U.S. application Ser. No. 15/059,366, filed Mar. 3, 2016, which is incorporated herein by reference in its entirety.

BACKGROUND

Field of the Invention

The present invention relates to lamina plate assemblies that are used as lamina support following laminectomy in cervical and lumbar cases.

Description of the Related Art

The performance of a spinal laminectomy without instrumentation can lead to spinal deformity after the procedure. When doing a laminectomy, the performing surgeon removes the posterior arch, which removes the fixation point for muscles to attach. As a result, the posterior tension band is lost and kyphosis can occur over time because the extensor muscles in the cervical and lumbar spine cannot maintain tension to keep the correct curvature.

Additionally, laminectomy with fusion is another posterior approach that decompresses the spinal cord, but does not lead to spinal destabilization as in the case with a laminectomy without fusion. However, if the surgeon does not use any product to protect the spinal cord, muscles may attach to the dura and scar tissue will form. Such epidural scarring can make it very difficult for a reoperation and can be irritating to some patients.

Further, some surgeons believe in a less invasive approach by preserving the posterior elements and performing a laminoplasty. However, with laminoplasty, surgeons are not able to achieve bilateral decompression as in the case with performing a laminectomy. In addition, the potential for the posterior arch to cave in on the implant and compress the spinal cord is a possibility.

Accordingly, there exists a need for a lamina plate assembly to protect the patient's spinal cord and to provide an attachment point or attachment points for muscles following laminectomy or laminoplasty to restore the posterior tension bands as well as to provide surgeons with another option to easily achieve direct decompression of the spinal cord with similar results as the more difficult laminoplasty procedure, as well as to restore the patient's posterior profile for cosmetic purposes.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, a lamina plate assembly may be configured to provide lamina support following laminectomy in cervical and lumbar cases. The lamina plate assembly may include a generally elongate body having a first free end, a second free end, and a posterior portion disposed between the first free end and the second free end. A first securing portion is connected to the first free end, away from the body, and a second securing portion is connected to the second free end, away from the body. Each of the first securing portion and the second securing portion includes an opening formed therein that is sized to allow a securing member to extend therethrough and secure each of the first securing portion and the second securing portion to a vertebra.

In one embodiment, the lamina plate assembly includes a generally U-shaped body having a first free end and a second free end, such that the body has at least one opening formed therein. A first securing foot is securable to the first free end and a second securing foot is securable to the second free end, such that the first securing foot and the second securing foot are each adapted to be secured to a vertebra.

In an alternative embodiment, the lamina plate assembly includes an elongate member having a first end, a second end, and a plurality of openings formed therethrough between the first end and the second end. The elongate member is bendable into a curved shape. A first securing member extends from the first end away from the body. The first securing member has at least one opening formed therethrough. A second securing member extends from the second end away from the body. The second securing member has at least one opening formed therethrough. A first securing device is adapted to be inserted through the at least one opening in the first securing member and a second securing device is adapted to be inserted through the at least one opening in the second securing member to secure the elongate member to a vertebra.

In still another alternative embodiment, the lamina plate assembly comprises a generally elongate body having a first leg portion, a second leg portion, and a posterior portion disposed between the first leg portion and the second leg portion. A first foot is adjustably connectable to the first leg portion and a second foot is adjustably connectable to the second leg portion such that each of the first foot and the second foot is adapted to secure each of the first leg portion and the second leg portion to a vertebra.

In yet another alternative embodiment, the lamina plate assembly comprises a generally U-shaped body having a first free end and a second free end. The body has at least one opening formed therein. A first securing foot is securable to the first free end and a second securing foot is securable to the second free end. The first securing foot and the second securing foot are each adapted to be secured to a vertebra.

In still another alternative embodiment, the lamina plate assembly comprises a generally arcuate lamina plate having a first leg and a second leg. A first foot is adapted to be inserted into the first leg such that the first foot adjustably secures the first leg to a vertebra and a second foot adapted to be inserted into the second leg, such that the second foot adjustably secures the second leg to the vertebra. The first foot comprises an insertion member and a locking member rotationally coupled to the insertion member. The first leg comprises a passage adapted to adjustably receive the insertion member such that the locking member is rotatable to secure the insertion member within the passage.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 2 is a top plan view of a static lamina plate assembly according to an exemplary embodiment;

FIG. 3 is a perspective view of the lamina plate assembly shown in FIG. 2, having been bent into an arcuate shape;

FIG. 10 is a top plan view of yet another alternative exemplary embodiment of the securing member for use with the lamina plate assembly shown in FIG. 2;

FIG. 11 is a perspective view of the lamina plate assembly shown in FIG. 9, with polyaxial screws inserted through either end thereof;

FIG. 12 is a bottom elevational view of a connection end of the lamina plate assembly shown in FIG. 8;

FIG. 12A is a sectional view of the connection end of the lamina plate assembly shown in FIG. 12;

FIG. 13 is a perspective view of a static lamina plate assembly according to another alternative exemplary embodiment;

FIG. 14 is a side elevational view of the lamina plate assembly shown in FIG. 13 having been bent to provide a smaller bend radius;

FIG. 15 is an enlarged perspective view of a connection portion of the lamina plate assembly shown in FIG. 13;

FIG. 17 is a perspective view of a lamina plate assembly according to still another alternative exemplary embodiment;

FIG. 18 is a sectional view of the lamina plate assembly shown in FIG. 17;

FIG. 23 is a perspective view of the lamina plate assembly shown in FIG. 17, with the foot shown in FIG. 22 attached thereto;

FIG. 24 is an enlarged perspective view of the free end of the lamina plate assembly with foot shown in FIG. 23;

FIG. 25 is a top plan view of a pre-formed alternative embodiment of a foot for use with the free end of the lamina plate assembly shown in FIG. 21;

FIG. 26 is a side elevational view of the fully formed foot shown in FIG. 25;

FIG. 34 is a perspective view of an adjustable lamina plate assembly according to another alternative exemplary embodiment, with the lamina plate assembly in an expanded condition;

FIG. 35 is a perspective view of the lamina plate assembly shown in FIG. 34, with the lamina plate assembly in a contracted condition;

FIG. 36 is a perspective view of an adjustable lamina plate assembly according to still another alternative exemplary embodiment, with the lamina plate assembly in a compressed condition;

FIG. 37 is a perspective view of the lamina plate assembly shown in FIG. 36, with the lamina plate assembly in an expanded condition;

FIG. 40 is a sectional view of the lamina plate assembly shown in FIG. 36, with the foot shown in FIG. 39, with the foot in an unlocked condition;

FIG. 41 is a sectional view of the lamina plate assembly shown in FIG. 36, with the foot shown in FIG. 39, with the foot in a locked condition;

FIG. 46 is a top plan view of the allograft lamina plate assembly shown in FIG. 43;

FIG. 47 is a sectional view of a femur segment used to make an alternative embodiment of an allograft lamina plate assembly;

FIG. 48 is a perspective view of the alternative embodiment of the allograft lamina plate assembly formed from the femur shown in FIG. 47;

FIG. 49 is a first sectional view of the allograft lamina plate assembly shown in FIG. 48;

FIG. 52 is a side elevational view of the allograft lamina plate assembly shown in FIG. 43;

FIG. 53 is a perspective view of a free end of the allograft lamina plate assembly shown in FIG. 43, with a foot shown in FIG. 22 inserted therein;

FIG. 54 is a side elevational view of a free end of an alternative embodiment of an allograft lamina plate assembly; and FIG. 55 is a perspective view of the free end of the allograft lamina plate assembly shown in FIG. 54, with a foot attached thereto.

DETAILED DESCRIPTION

Figure 1:
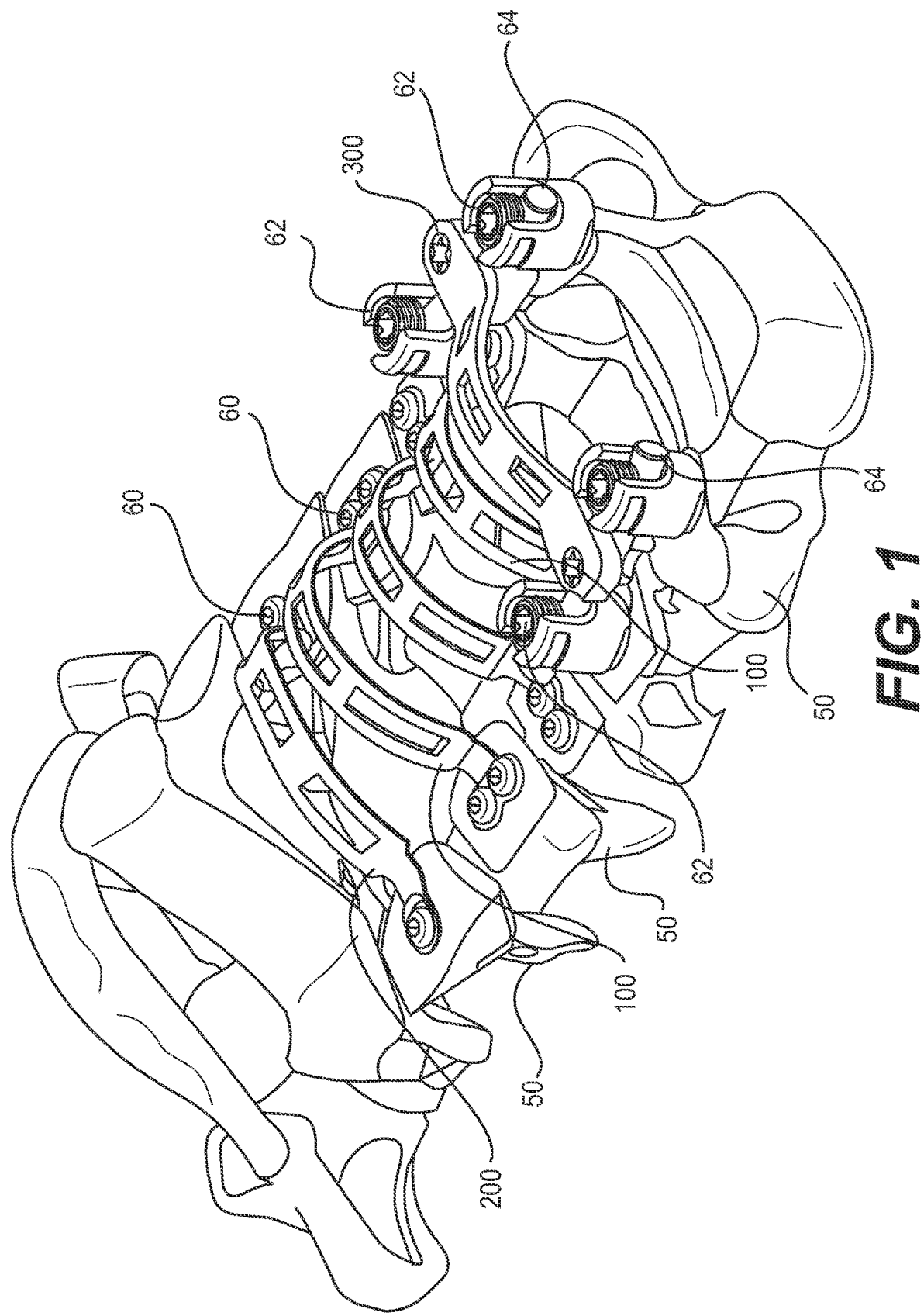
FIG. 1 is a perspective view of a plurality of embodiments of static lamina plate assemblies attached to individual vertebrae along a spinal column.

In the drawings, like numerals indicate like elements throughout. Certain terminology is used herein for convenience only and is not to be taken as a limitation on the present invention. The terminology includes the words specifically mentioned, derivatives thereof and words of similar import. The term "lateral" is intended to mean a direction away from the center of the vertebrae (e.g., about the spinous process) in the left or right direction of the patient; the term "posterior" is intended to mean a direction away from the center of the vertebra in the rear direction of the patient; and the term "anterior" is intended to mean a direction away from the center of the vertebra in the forward direction of the patient. When the term "about" is used with physical dimensions, the value attributed to such dimensions is +/−20% of the given dimension value. By way of example, "about 10 millimeters" is intended to mean a range between 8 millimeters and 12 millimeters.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The present disclosure provides embodiments of lamina plates that can be used to provide lamina support following a laminectomy. FIG. 1 shows different embodiments of static lamina plate assemblies 100, 200, 300 that are secured to a vertebra 50 or vertebrae 50 of a patient, such as, for example, the posterior portion of the spine exposed by a laminectomy. The lamina plate assemblies 100, 200, 300 may be secured with fasteners or pedicle screws, for example.

Static lamina plates are used as lamina support following a laminectomy in cervical and lumbar cases and can be used in standalone applications to preserve motion or applications with traditional CT or MCS systems to help promote fusion. The primary purpose of a lamina plate is to protect the spinal cord and to provide structure and an attachment point for muscles following a laminectomy to restore the posterior tension band. Secondary applications of static lamina plates are to provide surgeons another option to easily achieve direct decompression of the spinal cord with similar results to the more difficult laminoplasty procedure, and to restore the patient's posterior profile for cosmetic purposes. Prior to using the lamina plate, the surgeon performs a typical laminectomy. The lamina plate can then be quickly tacked on to the patient's spine for structure and protection.

The arched shape of static lamina plate assemblies 100, 200, 300 replace posterior elements (C3-L5) that connect to the lateral masses, as shown in FIG. 1. Assemblies 100, 200, 300 can be provided in various sizes to match the patient's particular anatomy. For particular standalone applications, as discussed below, assemblies 100, 200, 300 can have oblong, adjacent, or in-line holes, depending on the patient's anatomy, as well as the web segment that is being replaced. Additionally, for infusion cases, assemblies 100, 200, 300 can be provided with polyaxial screw holes for both cervical and lumbar segments, as well as for rod-to-rod connections.

Figure 4:
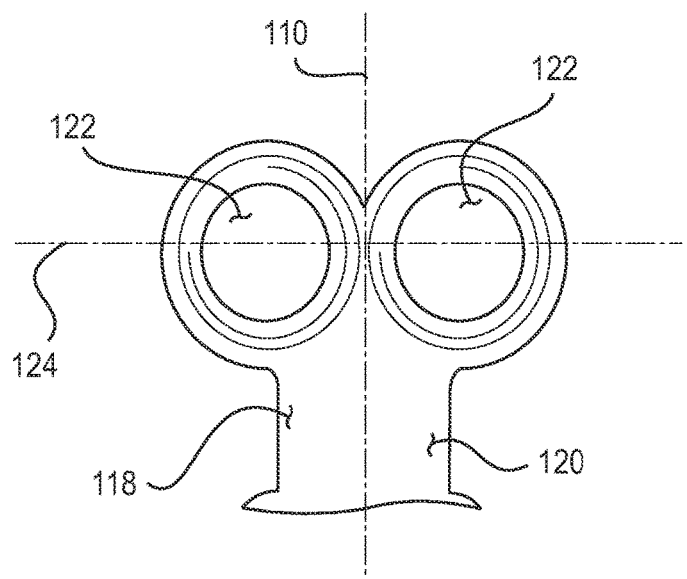
FIG. 4 is a top plan view of an exemplary embodiment of a securing member for use with the lamina plate assembly shown in FIG. 2.

According to one embodiment, shown in FIGS. 2-4, a lamina plate assembly 100 ("assembly 100") may include a generally elongate body 102 having a first free end 104, a second free end 106, disposed away from first free end 104, and a posterior portion 108 disposed between first free end 104 and second free end 106. In an exemplary embodiment, body 102 may be constructed from a biocompatible metal, such as, for example, commercially pure titanium, although those skilled in the art will recognize that body 102 can be constructed from other biocompatible materials as well. Titanium can be a desirable material because it has been shown to be a good material for tissue ongrowth. As a result, muscle can reattach to assembly 100 to reform the posterior tension band and to help maintain cervical or lumbar lordosis. Body 102 can be formed as a flat sheet, as shown in FIG. 2, and then bent into an arcuate or curved shape as desired, as shown in FIG. 3, according to the anatomy of the particular patient.

Body 102, with posterior portion 108, extends along a longitudinal axis 110. Posterior portion 108 also has side edges 112, 114 that extend in a straight line between first free end 104 and second free end 106 parallel to longitudinal axis 110 and to each other.

Further, posterior portion 108 of body 102 includes a plurality of through-openings, or "windows" 116 disposed between first free end 104 and second free end 106 that can be used as suture holes for surgically attaching muscles (not shown) to assembly 100 for more rigid fixation. Alternatively, windows 116 can be used to apply graft material (not shown) through assembly 100 and, still alternatively, windows 116 can be used to allow for bone growth therethrough after insertion into the patient. An additional advantage of windows 116 is to allow the surgeon to visualize the cervical and lumbar canal during surgery.

A first securing portion 118 is connected to first free end 104, and extends away from body 102. Similarly, a second securing portion 120 is connected to second free end 106, and extends away from body 102. Each of first securing portion 118 and second securing portion 120 includes an opening 122 formed therein sized to allow a securing member, such as, for example, a screw 60, shown in FIG. 1, to extend therethrough and secure each of the securing portion 118 and second securing portion 120 to vertebra 50 (e.g., at the lateral masses). Securing portions 118, 120 can be in the form of securing feet that are fixedly secured to first free end 104 and second free end 106, respectively.

Different embodiments of securing portions can be provided to secure assembly 100 to vertebra 50. The different embodiments provide different configurations that can be selected based on the patient's anatomy.

Exemplary embodiments of securing portions are shown FIGS. 4-7. Securing portions 118, 120, shown in FIGS. 2-4, each provide two adjacent generally circular openings 122 that extend along an axis 124 transverse to axis 110. Openings 122 are sized to accept screw 60 without any longitudinal or lateral adjustment of securing portions 118, 120.

Figure 5:
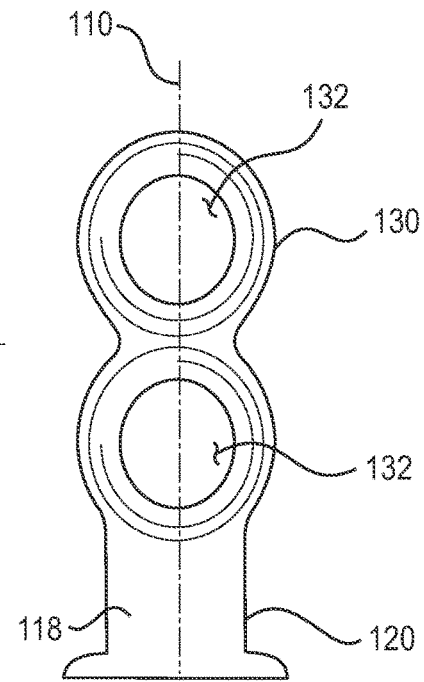
FIG. 5 is a top plan view of an alternative exemplary embodiment of the securing member for use with the lamina plate assembly shown in FIG. 2.

FIG. 5 shows a securing portion 130 having two adjacent generally circular openings 132 that extend coaxial with longitudinal axis 110. Similar to openings 122, openings 132 are sized to accept screw 60 without any longitudinal or lateral adjustment of securing portion 130.

Figure 6:
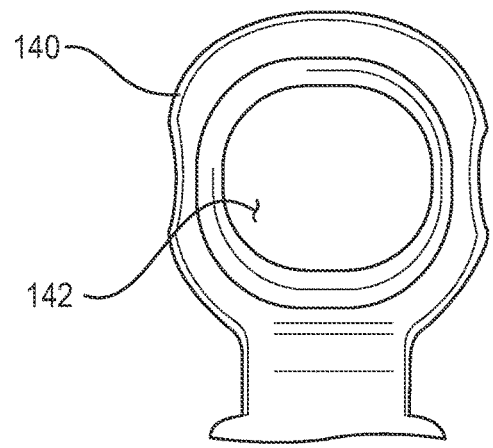
FIG. 6 is a top plan view of another alternative exemplary embodiment of the securing member for use with the lamina plate assembly shown in FIG. 2.
Figure 7:
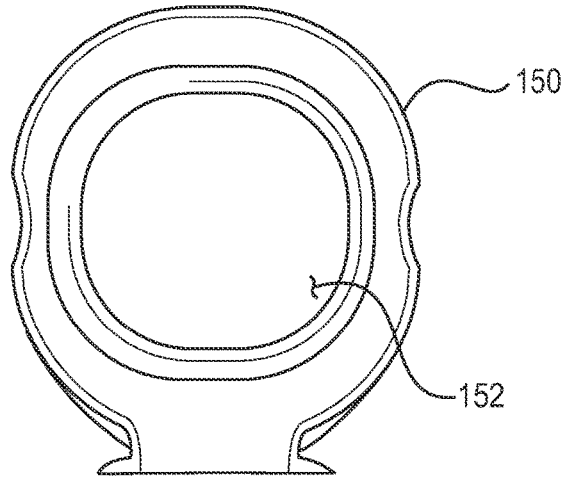
FIG. 7 is a top plan view of still another alternative exemplary embodiment of the securing member for use with the lamina plate assembly shown in FIG. 2.

FIG. 6 shows an alternative embodiment of a securing portion 140 having a single opening 142 sized to accept a small polyaxial screw 62 (shown in FIG. 1). FIG. 7 shows still another alternative embodiment of the securing portion 150 having a single opening 152 sized to accept a large polyaxial screw (not shown).

Referring back to FIGS. 2 and 3, in the exemplary embodiment where assembly 100 is constructed from a metal, or other malleable material, assembly 100 can be machined from a flat sheet and posterior portion 108 can then be bent from the straight configuration shown in FIG. 2 to the bent configuration of the arcuate shape shown in FIG. 3 as required to match the particular patient's posterior anatomy.

While, in most cases, a straight assembly 100 as discussed above can be used, at levels in which a preserved posterior arch is obstructing the space, angled lamina plates can be used to decompress the space and avoid existing posterior arch segment. Consequently, in an alternative embodiment of a static lamina assembly 200 ("assembly 200"), shown in FIGS. 1, 8, and 9, instead of having straight edges 112, 114 as shown in assembly 100 above, a posterior portion 208 of assembly 200 is an elongate member that initially extends in a plane (shown in FIG. 8) and has a first edge 212 and a second free edge 214 that both extend to form an arcuate portion between first free end 204 and second free end 206, which results in an angled assembly 200 when assembly 200 is bent to the condition shown in FIGS. 1 and 9. Assembly 200 can be used on patients in which a preserved posterior arch is obstructing installation of assembly 100.

Figure 9:
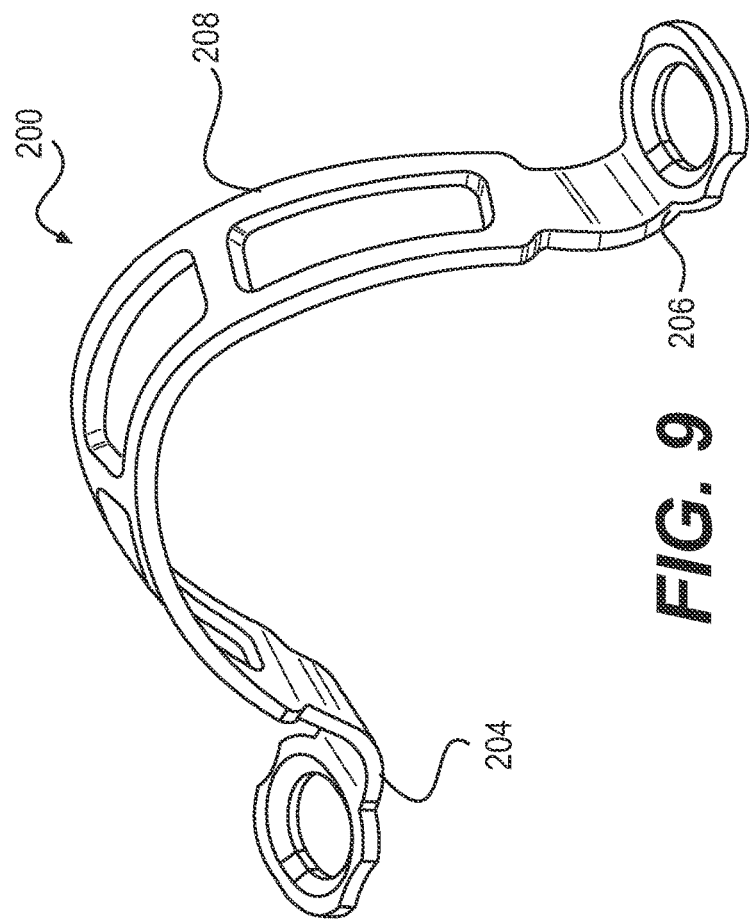
FIG. 9 is a perspective view of the lamina plate assembly shown in FIG. 8, having been bent into an arcuate shape.
Figure 8:
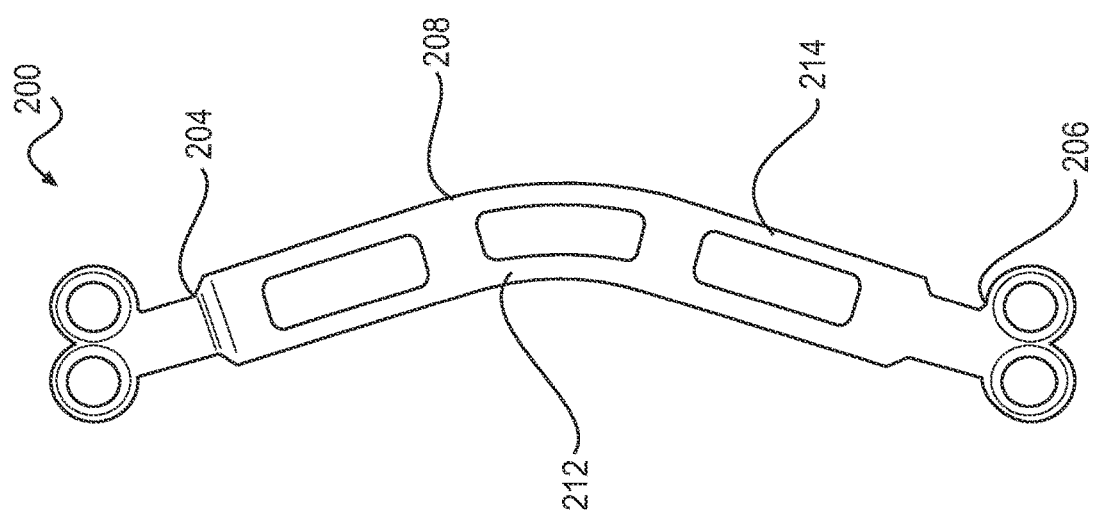
FIG. 8 is a top plan view of a static lamina plate assembly according to an alternative exemplary embodiment.

While assembly 200 is shown in FIGS. 8 and 9 as having securing portion 120 as shown in FIG. 4, assembly 200 (as well as assembly 100), can have securing portion 220 as shown in FIGS. 1 and 10, incorporating a generally oblong opening 222 that allows for lateral adjustment of assembly 200 or assembly 100, as desired or needed by the inserting surgeon. Further, while assembly 200 incorporates securing portion 220 as shown in FIG. 10, those skilled in the art will recognize that both assembly 100 and assembly 200 can incorporate any of the securing portions shown in FIGS. 4-10. For example, FIG. 11 shows assembly 200 being used with polyaxial screws 62.

As shown in FIG. 12, using securing portion 120 as an example, each of the first and second securing portions described above can include a ridge 160 extending outwardly from a bottom surface 158 of securing portion 120. Each ridge 130 is adapted to lag the first securing foot and the second securing foot into vertebra 50. Ridge 160 is used to help with internal fixation prior to screw placement and four fixation post-screw placement to help lag the particular assembly 100, 200 into vertebra 50. Such feature allows assembly 100, 200 to sink into the bone of vertebra 50 and to promote fusion between assembly 100, 200 and the surface of the bone for more rigid fixation.

While ridge 160 is shown in FIG. 12 as generally following along the outer perimeter of the securing portion, those skilled in the art will recognize that ridge 160 can be located anywhere along bottom surface 158, and can be broken into a plurality of separate ridges or can be the single ridge 160 as shown.

Referring back to FIG. 1, as well as to FIGS. 13-15, a lamina plate assembly 300 ("assembly 300") can be used with a rod 64 and polyaxial screws 62 two fuse adjacent vertebrae 50 to each other. Assembly 300 can be provided with a body 302 having a slight bend or curvature, as shown in FIG. 13. Alternatively, body 302 can have a more pronounced bend or curvature, as shown in FIG. 14, depending upon the anatomy of the particular patient.

While assembly 300 includes a first free end 304 and a second free end 306, each extending away from body 302, a securing member 308 extends outwardly from first end 304 and a securing member 310 extends outwardly from second end 306. Each securing member 308, 310 has a threaded hole 312 extending therethrough to accommodate a screw 314 for securing assembly 300 to rod 64. Securing portions 318, 320 extend underneath securing members 308, 310, respectively, to help retain rod 64 between securing portion 318 and securing member 308, as well as between securing portion 320 and securing member 310, respectively.

In addition to static lamina assemblies 100, 200, 300 as discussed above, FIG. 16 shows adjustable lamina assemblies 400, 400', 500, 600 that can be used as lamina support following a laminectomy. Similar to the static lamina assemblies 100, 200, 300, discussed above, adjustable lamina assemblies 400, 400', 500, 600 are constructed from a biocompatible metal, such as, for example, titanium, and have an arched shape to replace the posterior elements (C3-L5). Adjustable lamina assemblies 400, 500, 600 have adjustable bodies, as well as adjustable securing feet that are slidingly insertable into free ends of each assembly 400, 500, 600, such that the bodies and the securing feet can both be adjusted according to the patient's particular anatomy. Lamina assemblies 400, 500, 600 may be provided separate from the securing feet or, alternatively, preassembled with the feet. The adjustable lamina assemblies can be adjusted to various sizes to match the particular patient anatomy.

Figure 19:
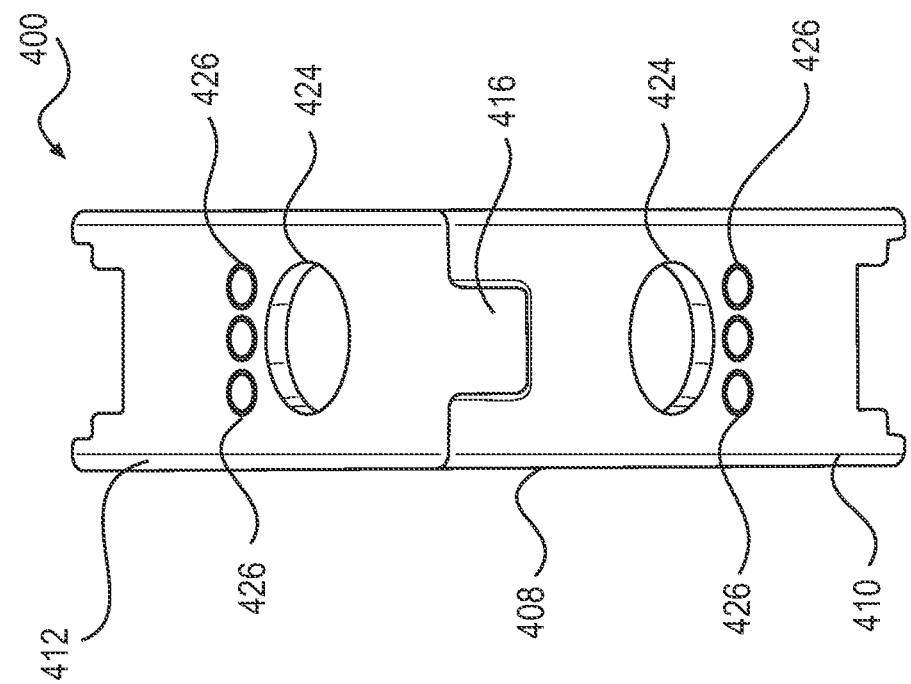
FIG. 19 is a top plan view of the lamina plate assembly shown in FIG. 17.

Adjustable lamina assembly 400 ("assembly 400"), shown in FIGS. 17-19, has a generally U-shaped body 402 having a first free end 404, a second free end 406, and a posterior portion 408, extending between first free end 404 and second free end 406. Posterior portion 408 comprises a generally hollow first portion 410 and a generally hollow second portion 412. In an exemplary embodiment, first portion 410 comprises a female connector 414 and second portion 412 comprises a male connector 416 connected to female connector 414. A pivot set screw 418 (shown in detail in FIG. 20) pivotally connects male connector 416 to female connector 414, allowing for adjustment of female connector 414 with respect to male connector 416, according to patient needs.

Set screw 418 includes a threaded end 419 that threads into female connector 414, allowing assembly 400 to be locked in a particular desired width by tightening set screw 418 to pull female connector 414 against male connector 416, locking assembly 400 in place. Optionally, instead of threaded set screw 418, an unthreaded pin (not shown) can be used to hingedly connect female connector 414 to male connector 416, but without the ability to lock assembly 400 at a desired width.

Figure 20:
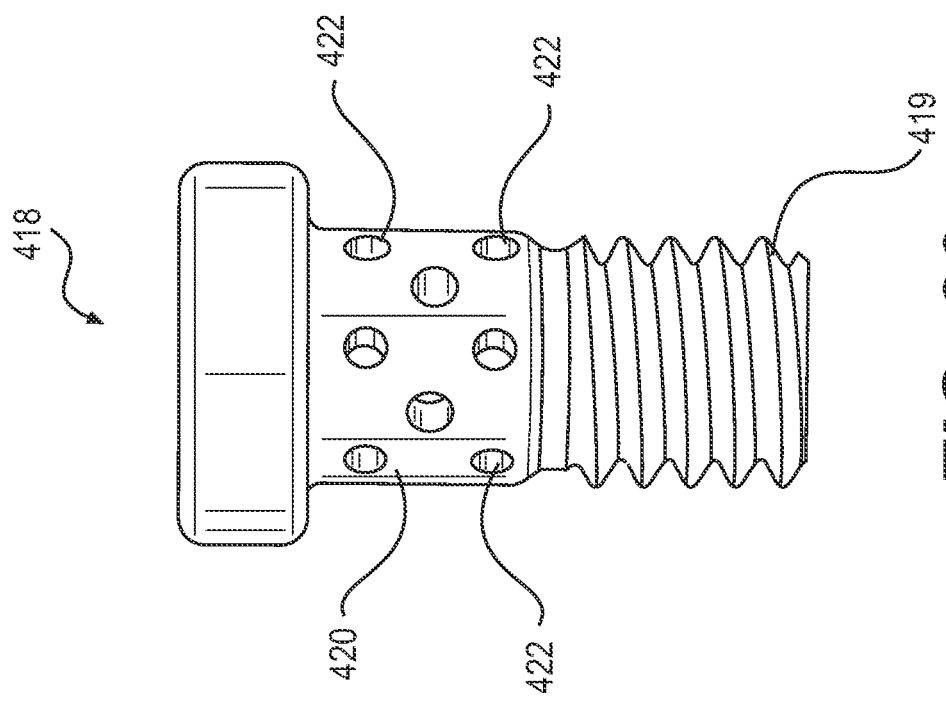
FIG. 20 is a side elevational view of a screw used with the lamina plate assembly shown in FIG. 17.

Referring to FIG. 20, screw 418 includes a hollow body 420 and a plurality of through openings 424, 426 extending through body 420. The hollow feature of body 420 allows bone to grow through openings 424, 426 and into body 420 to fix assembly 400 in its inserted condition.

Referring in particular to FIG. 19, each of first portion 410 and second portion 412 includes at least one graft window 424 that can be used to insert a graft material (not shown) into each of first portion 410 and second portion 412. Additionally, each of first portion 410 and second portion 412 includes at least one suture hole 426 formed therein to allow the surgeon to suture down muscles (not shown) to assembly 400 for more rigid fixation. Such extra fixation can aid in muscle reattachment to help reform the posterior tension band.

Figure 21:
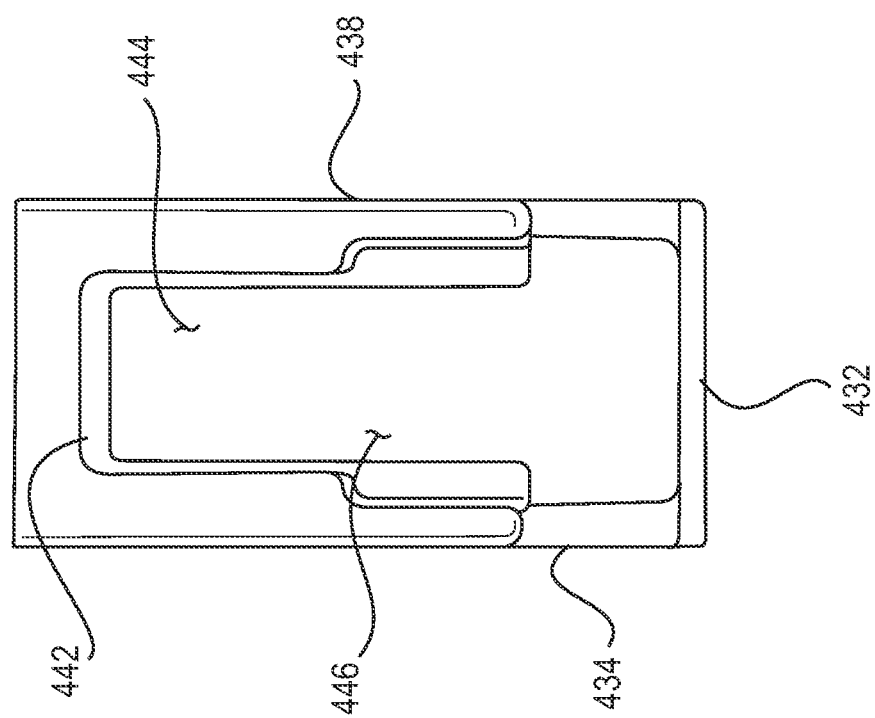
FIG. 21 is a side elevational view of a free end of the lamina plate assembly shown in FIG. 17.

Referring to FIGS. 17, 18, and 21, first free end 404 includes a first leg portion 430 having a rear wall 432 and a first side wall 434 extending laterally from rear wall 432. Rear wall 432 includes an extension 433 projecting away from posterior portion 408. Extension 433 allows the implanting surgeon to size the appropriate assembly 400 and to bump up against the patient's lateral mass for enhanced placement of assembly 400.

First side wall 434 includes a first locking slot 436 formed therein. Similarly, a second side wall 438 extends laterally from rear wall 432 and parallel to first side wall 434. Second side wall 438 has a second locking slot 440 formed therein. First leg portion 430 also includes a front wall 442 having a window 444 formed therein. Window 444 allows the implanting surgeon to unlock foot 450 in the case where a different foot is required.

Figure 16:
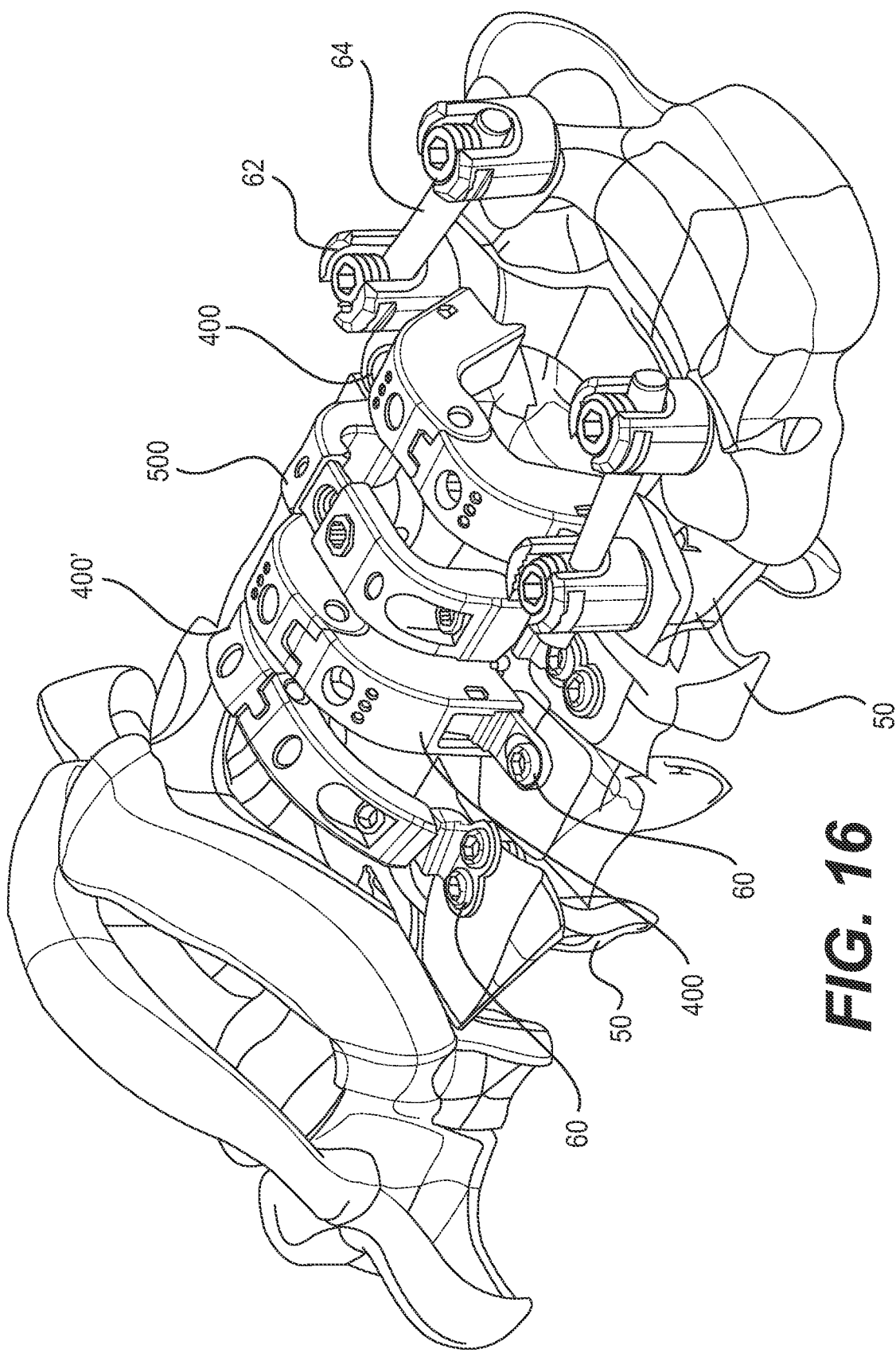
FIG. 16 is a perspective view of a plurality of alternative embodiments of adjustable lamina plate assemblies attached to individual vertebrae along a spinal column.

Rear wall 432, first and second side walls 434, 438, and front wall 442 together define a receiver, such as a slot 446, shown in FIG. 21, into which an adjustable foot 450 can be inserted. Correspondingly, assembly 400 includes a pair of adjustable feet 450 that are securable to each of first free end 404 and second free end 406, such that securing feet 450 are each adapted to be secured to vertebra 50, as shown in FIG. 16.

Figure 22:
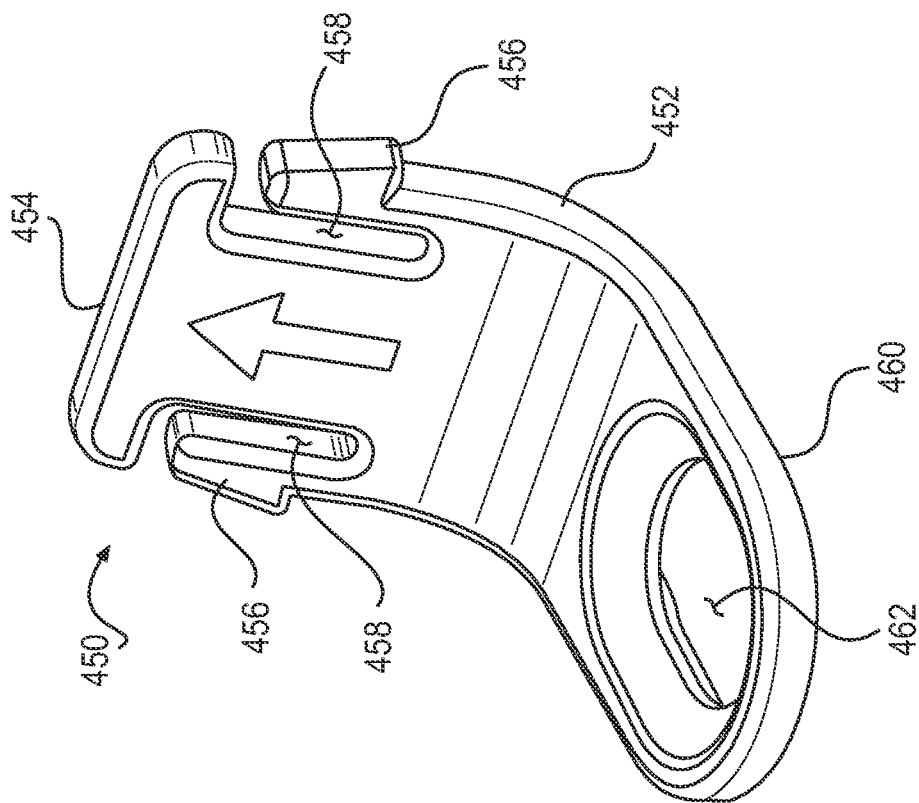
FIG. 22 is a perspective view of an exemplary embodiment of a foot used with the free end of the lamina plate assembly shown in FIG. 21.

In an exemplary embodiment, referring to FIG. 22, foot 450 includes a planar first end 452 having a tab 454 sized to slidingly fit into slot 446. First end 452 further comprises a wing 456 extending outwardly from opposing sides thereof. Each wing 456 is adapted to extend into first and second locking slots 436, 440, respectively. First end 452 further comprises a relief 458 proximate to each wing 456 such that, as first end 452 is inserted into locking slots 436, 440, relief 458 allows wing 456 to bias toward relief 458 such that the wings 456 are insertable into slots 436, 440. Each relief 458 has an open top portion to provide flexibility for wings 456. When each wing 456 engages a respective locking slot 436, 440, each relief 458 biases each respective wing 456 into its respective locking slot 436, 440, releasably securing foot 450 to first leg portion 404 and second leg portion 406, as shown in FIGS. 23 and 24. Foot 450 can be removed from assembly 400 by inserting a removal tool (not shown) into locking slots 436, 440 to bias wings 456 inwardly toward each other, and then sliding foot 450 outwardly from slot 446.

Foot 450 also includes a second end 460 having an opening 462 formed therein. Opening 462 is sized to allow a securing member 60 (shown in FIG. 16) to extend therethrough such that securing member 60 secures foot 450 to vertebra 50.

In an exemplary embodiment, feet 450 are constructed from a malleable biocompatible material, such as, for example, titanium, that allows first end 452 to be bent relative to second end 460, depending on the anatomy of the particular patient. By way of example only, foot 450 can be initially manufactured as a generally flat member, and, prior to installation with assembly 400, as shown in FIG. 22, first end 452 can be bent at an angle of about 90° relative to second end 460.

As shown in FIGS. 25 and 26, a foot 450', similar to foot 450, can be provided with assembly 400 instead of foot 450. Foot 450' has a closed relief portion 458' instead of the open relief portion 458 in foot 450, and also includes an elongate opening 462' in second end 460' to accommodate a polyaxial screw (not shown). Foot 450' can be inserted into slot 446 in assembly 400 in the same manner as described above with respect to foot 450.

Figure 27:
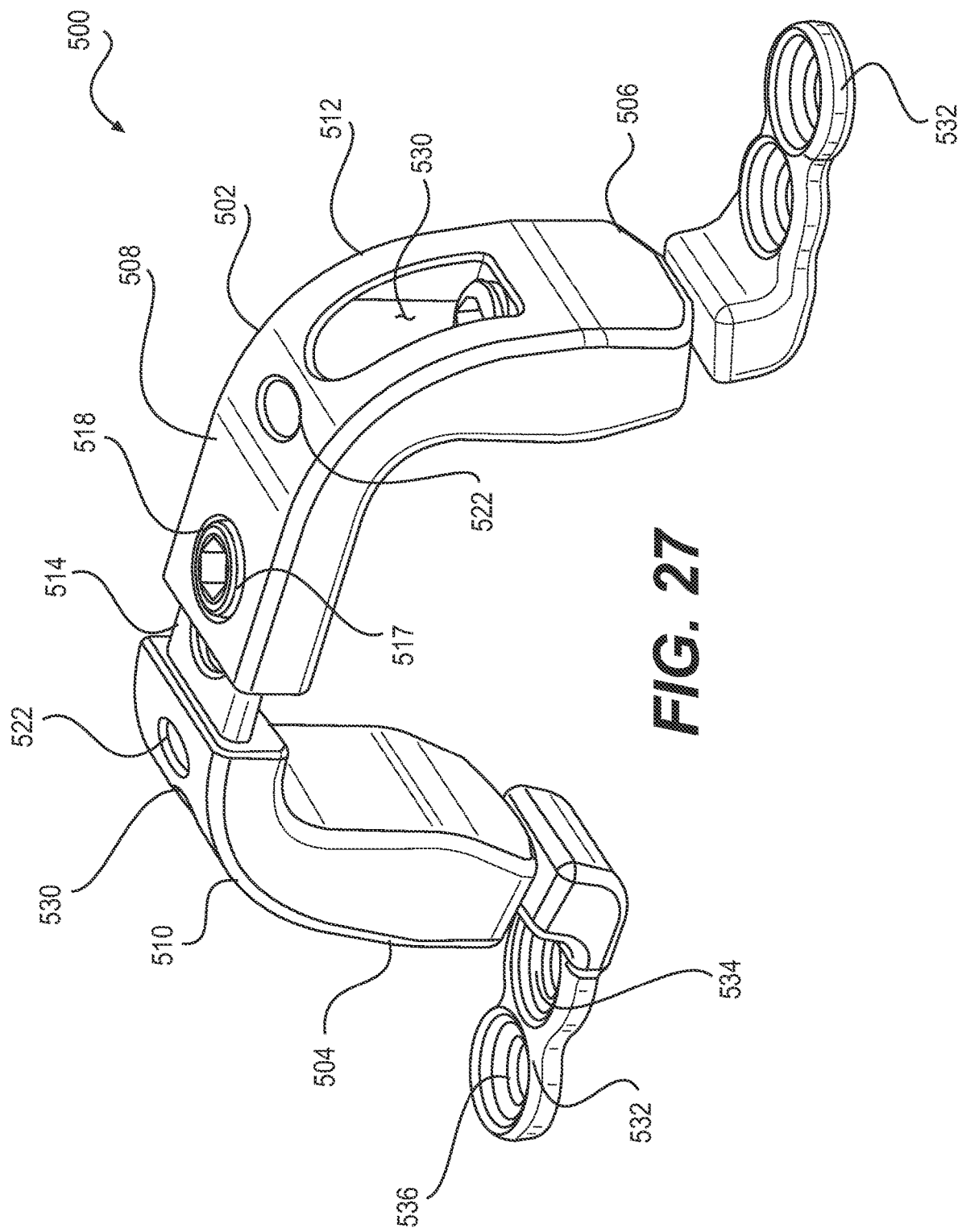
FIG. 27 is a perspective view of a lamina plate assembly according to yet another alternative exemplary embodiment.
Figure 28:
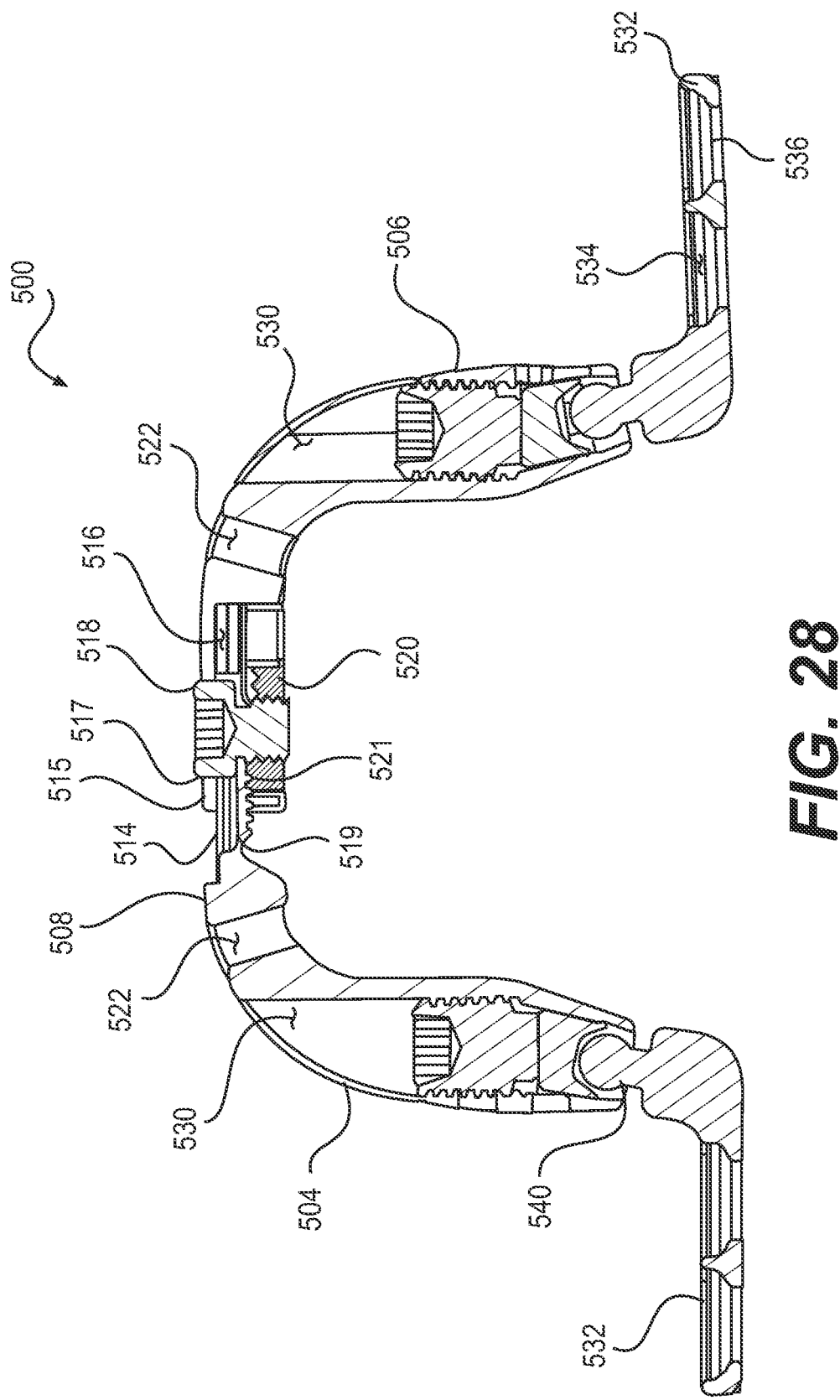
FIG. 28 is a sectional view of the lamina plate assembly shown in FIG. 27.
Figure 29:
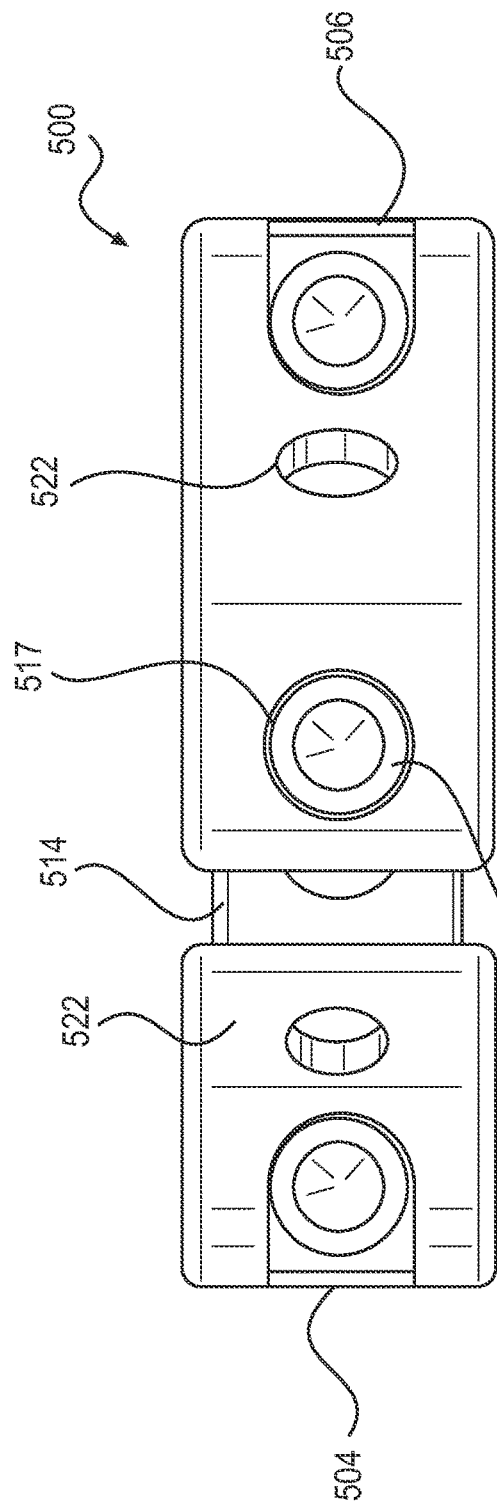
FIG. 29 is a top plan view of the lamina plate assembly shown in FIG. 27, shown in an expanded state.
Figure 30:
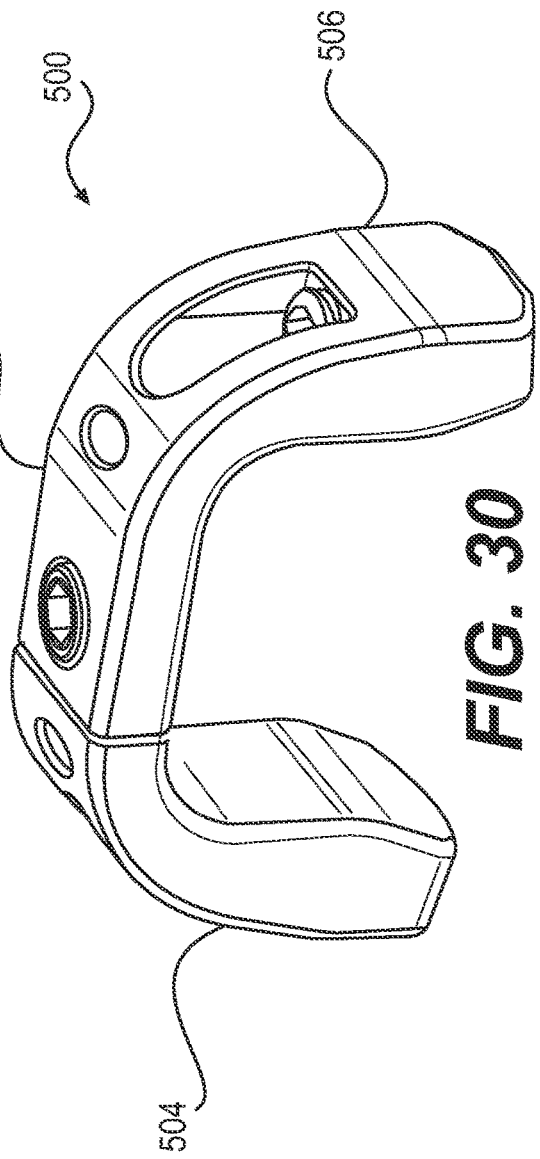
FIG. 30 is a perspective view of the lamina plate assembly shown in FIG. 27, shown in a compressed state.

An alternative embodiment of an adjustable lamina plate assembly 500 ("assembly 500") is shown in FIGS. 27-33. Assembly 500 has a generally U-shaped body 502 having a first free end 404, a second free end 506, and a posterior portion 508, extending between first free end 504 and second free end 506. Posterior portion 508 comprises a generally hollow first portion 510 and a generally hollow second portion 512. In an exemplary embodiment, first portion 510 comprises a male connector 514 having an elongate slot 515 and second portion 512 comprises a female connector 516 having a generally circular slot 517. A bottom surface of male connector 514 includes ribs 519. Male connector 514 is slidably insertable into female connector 516. A set screw 518 is inserted through generally circular slot 517 and elongate slot 515 to slidingly connect male connector 514 to female connector 516. Elongate slot 515 allows for lateral adjustment of female connector 516 with respect to male connector 514, according to patient needs. A nut 520 secures set screw 518 within slots 515, 517 to secure male connector 514 to female connector 516. A top surface of nut 520 includes ribs 521 that engage with ribs 519 on male connector 514 to secure male connector 514 to female connector 516. FIG. 27 shows assembly 500 with male connector 514 extending exteriorly from second portion 512, whereas FIG. 30 shows second portion 512 butted up against first portion 510.

Each of first portion 510 and second portion 512 includes at least one suture and visualization window 522 that can be used to give the surgeon the option of suturing down muscles to assembly 500 for more rigid fixation. This extra fixation may aid in muscle reattachment to help reform the patient's posterior tension band.

Each of first free end 504 and second free end 506 includes a through passage 530 having an anterior opening and an opposing posterior opening extending therethrough for the securement of an adjustable foot 532 thereto. As shown in FIGS. 27-29, similar to securing portion 130 shown in FIG. 5, two adjacent generally circular openings 534, 536 are provided in each foot 532 for a screw 60 to secure foot 532 to vertebra 50 (e.g., at the lateral masses), as shown in FIG. 16.

Figure 31:
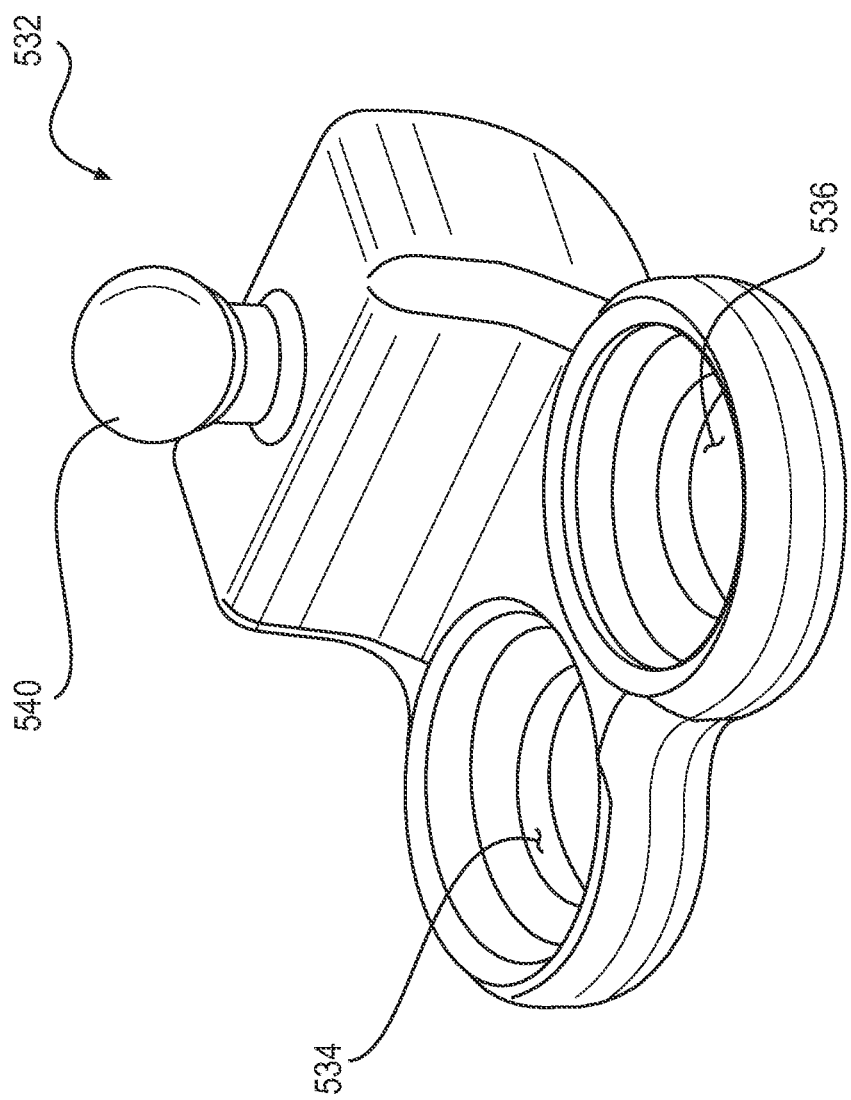
FIG. 31 is a perspective view of a foot for use with the lamina plate assembly shown in FIG. 27.
Figure 33:
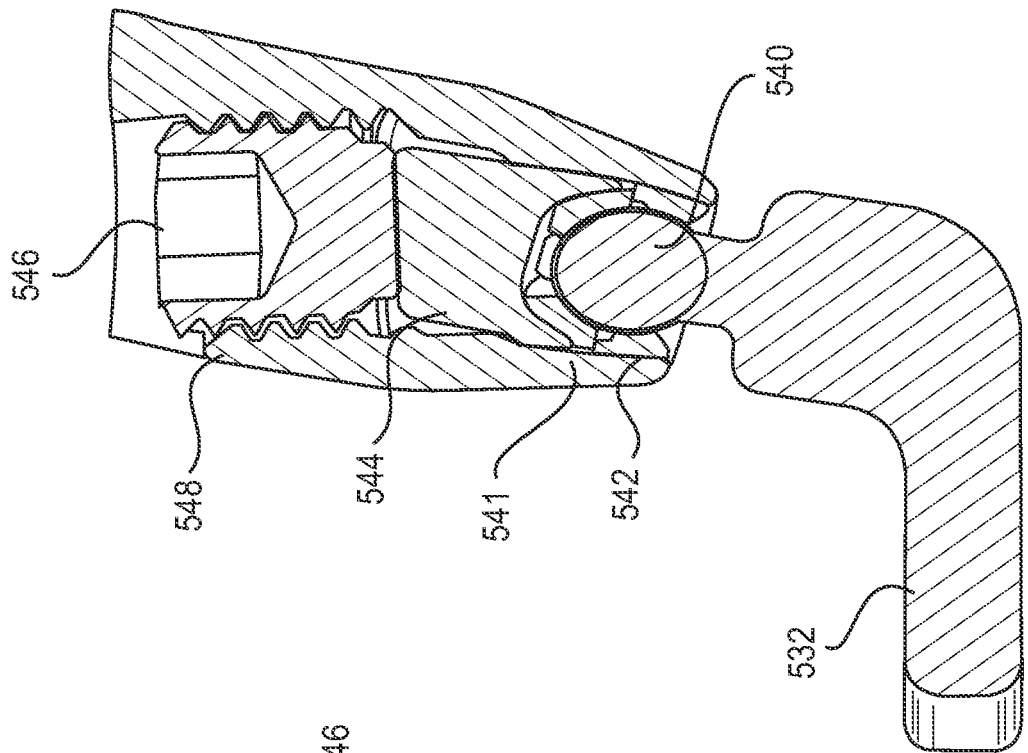
FIG. 33 is a sectional view of the foot shown in FIG. 31, fully inserted into the lamina plate assembly shown in FIG. 27.
Figure 32:
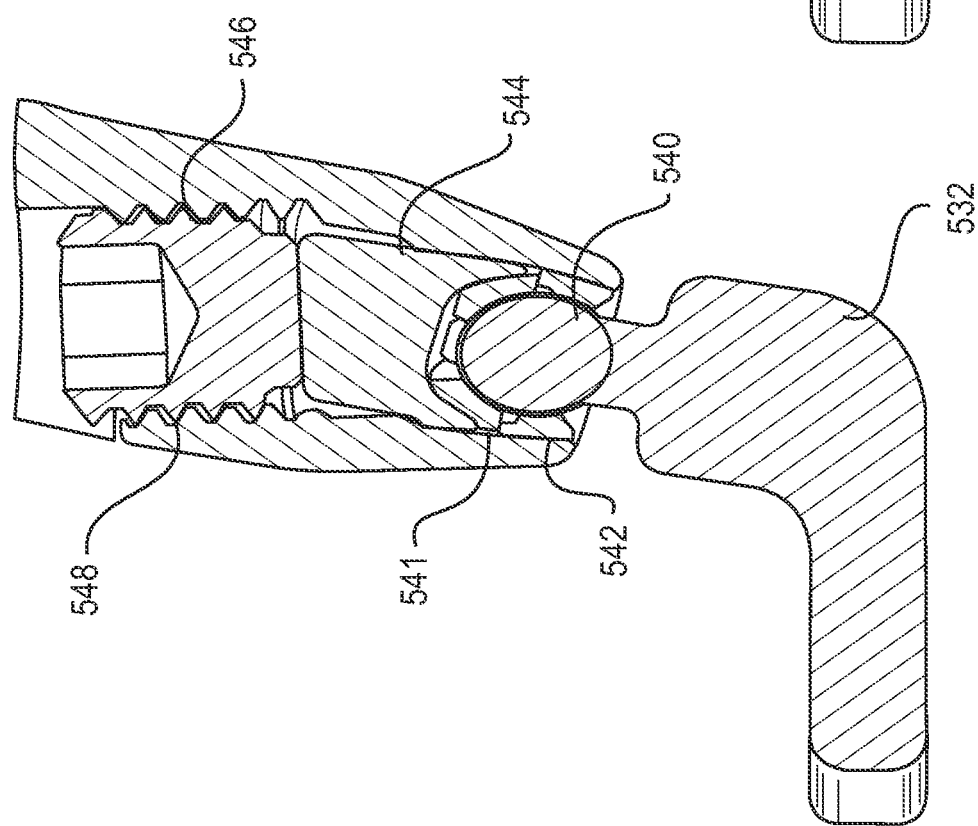
FIG. 32 is a sectional view of the foot shown in FIG. 31, partially inserted into the lamina plate assembly shown in FIG. 27.

Referring to FIG. 31, each foot 532 includes an insertion member in the form of a generally spherical polyaxial head 540 that is inserted into first free end 504 and second free end 506, respectively. Polyaxial head 540 allows for 40° of conical angulation, allowing assembly 500 to angle up to 20° in any direction, resulting in an infinite adjustment of foot 532 with respect to each of free end 504, 506. Referring to FIGS. 32 and 33, an anterior end 541 of passage 530 includes a securing device comprised of a clamp portion 542 that receives head 540 and a saddle 544. Saddle 544 is disposed posteriorly over clamp portion 542 and is used as a wedge by a locking member, such as a set screw 546, to secure clamp portion 542 over head 540. A posterior end 548 of passage 530 is threaded for engagement with set screw 546. In an unlocked condition, as shown in FIG. 32, saddle 544 is spaced away from clamp portion 542, allowing spherical head 540 to rotate within clamp 542. In a locking condition, as shown in FIG. 33, set screw 546 has been rotated to extend anteriorly, biasing saddle 544 against clamp 542, which in turn clamps clamp portion 542 over head 540, thereby securing spherical head 540 within clamp portion 542, locking foot 532 in place.

While assembly 500 is shown in FIGS. 27 and 28 as being used with foot 532, those skilled in the art will recognize that feet 532 can be used, with slight modifications, with assembly 400, as shown without foot 532 in modified assembly 400', in FIGS. 34 and 35. Assembly 400' provides the ability to pivot first portion 410' relative to first portion 412' about set screw 418, while still maintaining to advantages of polyaxial feet 532.

An alternative embodiment of an adjustable lamina plate assembly 600 ("assembly 600") is shown in FIGS. 36-41. Assembly 600 provides the ability to adjust the amount of decompression afforded there with. The adjustability of assembly 600 allows the surgeon to either freely adjust the anterior-posterior height of assembly 600 and locks assembly 600 in place, or to continuously elevate the height of assembly 604 control decompression. Assembly 600 can be used in standalone or fusion constructs, as with adjustable assemblies 400, 500 described above.

Figure 38:
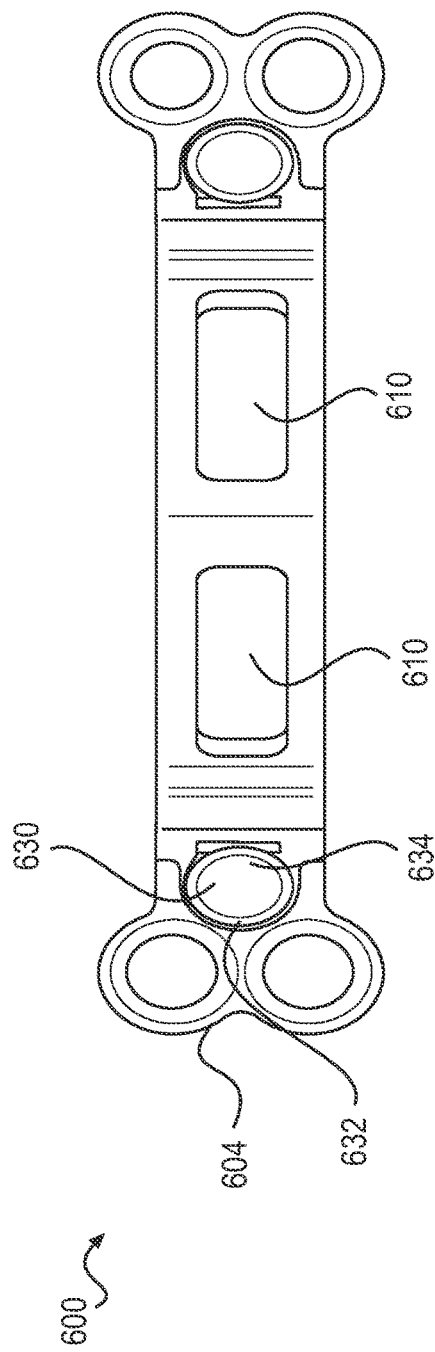
FIG. 38 is a top plan view of the lamina plate assembly shown in FIG. 36.

Assembly 600 includes a generally "U-shaped" body 602 having a first leg portion 604, a second leg portion 606, and a posterior portion 608 connecting first leg portion 604 and second leg portion 606. Referring specifically to FIG. 38, posterior portion 608 includes a plurality of visualization and suture windows 610 formed therein, that allow the surgeon to suture local muscles to assembly 600 for increased muscle fixation, which may result in promoting muscle reattachment to assembly 600 to help form the patient's posterior tension band.

Referring to FIGS. 37 and 40-41, each of first leg portion 604 and second leg portion 606 comprises a generally rectangular through-passage 620 having an anterior opening 622 and an opposing posterior opening 624. A rotational securing, or locking, member 630 extends laterally from rectangular through-passage 620 on first leg portion 604 and is used to releasably secure an adjustable foot 604 to first leg portion 604. Similarly, a locking member 630 is used to secure an adjustable foot 642 to second leg portion 606. Through-passage 620 and locking member 630 are used to support and secure adjustable feet 640, 642 that can be longitudinally adjusted to adjust the posterior height of assembly 600 between a compressed position, as shown in FIG. 36, and an extended position, as shown in FIG. 37.

As shown in FIGS. 36 and 37, feet 640, 642 having two different securing configurations, similar to the securing portions shown in FIG. 4 and FIG. 5, respectively, can be provided with assembly 600, as desired, depending upon the configuration of vertebra 50 of the particular patient. The connecting portions of each foot 640, 642 with respect to body 602 are the same, and will be described below with respect to first foot 640. Feet 640, 642 are able to be adjusted independently from each other to allow the surgeon optimal decompression to fit a particular patient's anatomy.

Figure 39:
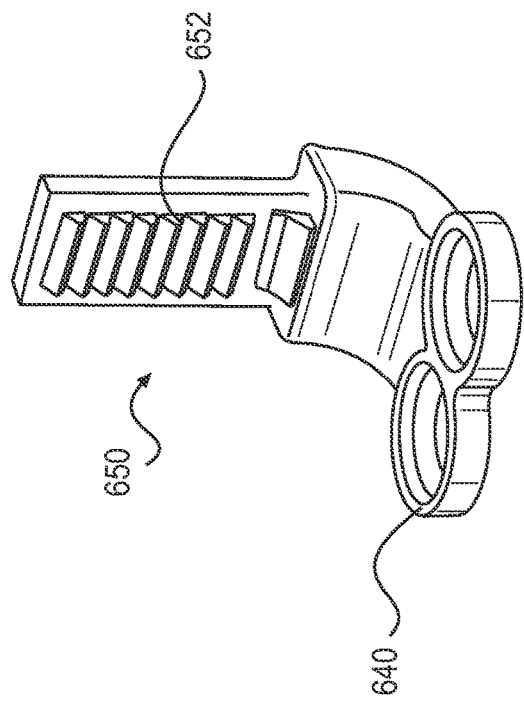
FIG. 39 is a perspective view of a foot for use with the lamina plate assembly shown in FIG. 36.

Referring to FIG. 39, first foot 640 includes a tang 650 that is insertable into through-passage 620. Tang 650 includes a plurality of laterally facing ribs 652, such that locking member 630 is rotatable to engage ribs 652 and secure first foot 640 to first leg portion 604.

Referring to FIGS. 40 and 41, securing member 630 has an arcuate rib portion 632 that is adapted to engage laterally facing ribs 652 of tang 650, as shown in FIG. 41, and a flat portion 634 adjacent to arcuate rib portion 632 that is adapted to disengage securing member 630 from ribs 652, as shown in FIG. 40.

While straight ribs 652 are shown, which allow for discrete height adjustments, those skilled in the art will recognize that, instead of straight ribs 52, angle ribs (not shown) can also be provided, resulting in a worm gear drive to provide for continuous expansion.

First leg portion 604 has a lateral window 660 formed therein with a lower lip 662 that extends into through-passage 620. Tang 650 includes a locking member 654 that is adapted to bias into lateral window 660. A biasing member 656, such as, for example, a spring, that biases locking member 654 outwardly from tang 650. As tang 650 is inserted into through-passage 620 from anterior opening 622 toward posterior opening 624, when locking member 654 passes lower lip 662, biasing member 656 biases locking member 654 into lateral window 660. Lower lip 662 then prevents tang 650 from being able to move anteriorly with respect to first leg portion 604, securely retaining tang 650 into first leg portion 604. In the event that it is desired to remove tang 650 from leg portion 604, locking, member 654 can be manually depressed through lateral window 660 to override lower lip 662 for removal.

Posterior portion 608 can be adjusted anteriorly/posteriorly with respect to feet 640, 642 by sliding first leg portion 604 and second leg portion 606 along tang 650 of each foot 640, 642, respectively. When posterior portion 608 is at a desired height relative to feet 640, 642, securing member 630 is rotated from the unlocked position shown in FIG. 40 to the locked position shown in FIG. 41, wherein arcuate rib portion 632 engages ribs 652 on tang 650, releasably securing posterior portion 608 to feet 640, 642.

In addition to static lamina assemblies 100, 200, 300 and adjustable lamina assemblies 400, 400', 500, 600 as discussed above, FIG. 42 shows allograft lamina assemblies 700, 800, 900 that can be used as lamina support following a laminectomy.

Figure 44:
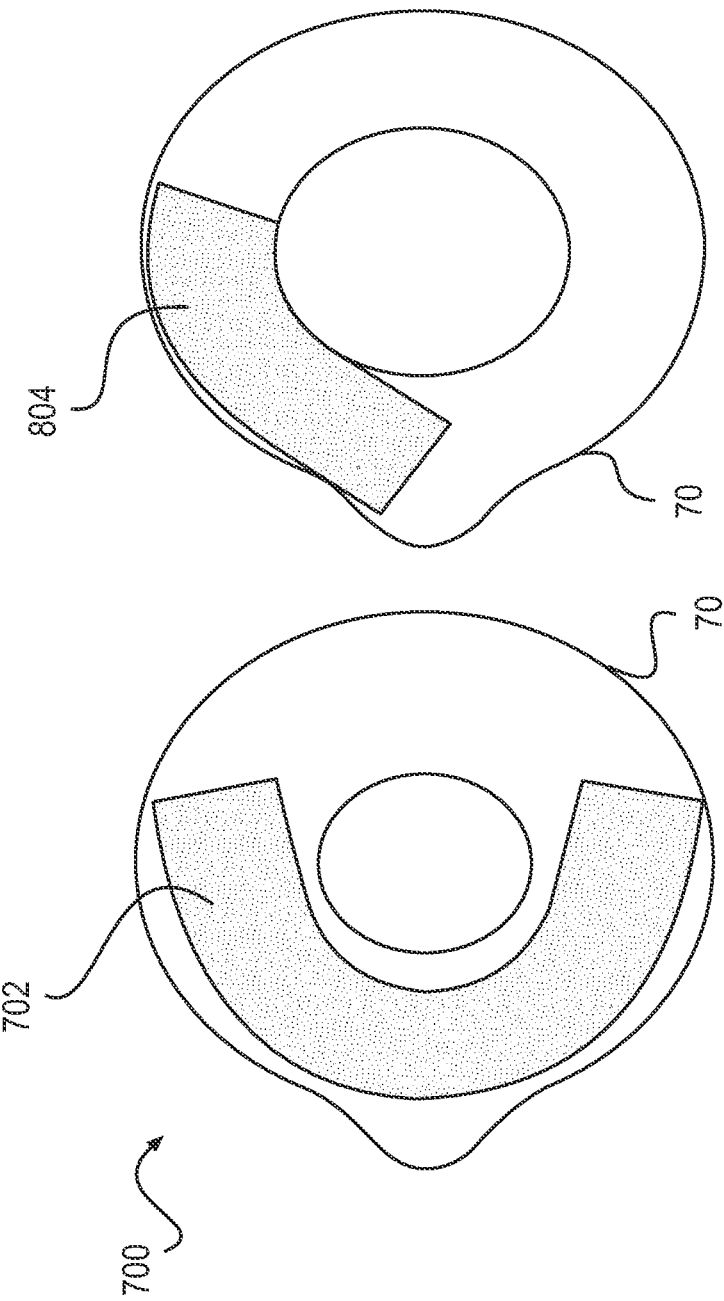
FIG. 44 is a sectional view of a femur segment used to make the allograft lamina plate assembly shown in FIG. 43.

Allograft lamina assembly 700 ("assembly 700"), shown in FIGS. 43-46, includes a body 702 that is constructed from human cortical bone. A benefit of using cortical bone is that the cortical bone allows tissue to reattach to assembly 700, as if assembly 700 was the patient's own bone. As a result, the patient's muscles should reattach to assembly 700 and reform the patient's posterior tension band to help maintain cervical or lumbar lordosis. As shown in FIG. 44, depending on the size of assembly 700, body 702 can be single piece, generally U-shaped body machined from a femur segment 70.

Assembly 700 includes a first free end 704, a second free end 706, and a posterior portion 708 extending between first free end 704 and second free end 706. Optionally, each of first free end 704 and second free end 706, can have the same connections as first free end 404 and second free end 406 in assembly 400 discussed above in order to accommodate feet 450 and 450', as shown in FIGS. 22 and 26, respectively. While assembly 700 is constructed from cortical bone, feet 450 and 450' can be constructed from a biocompatible metal, such as, for example, titanium.

Figure 45:
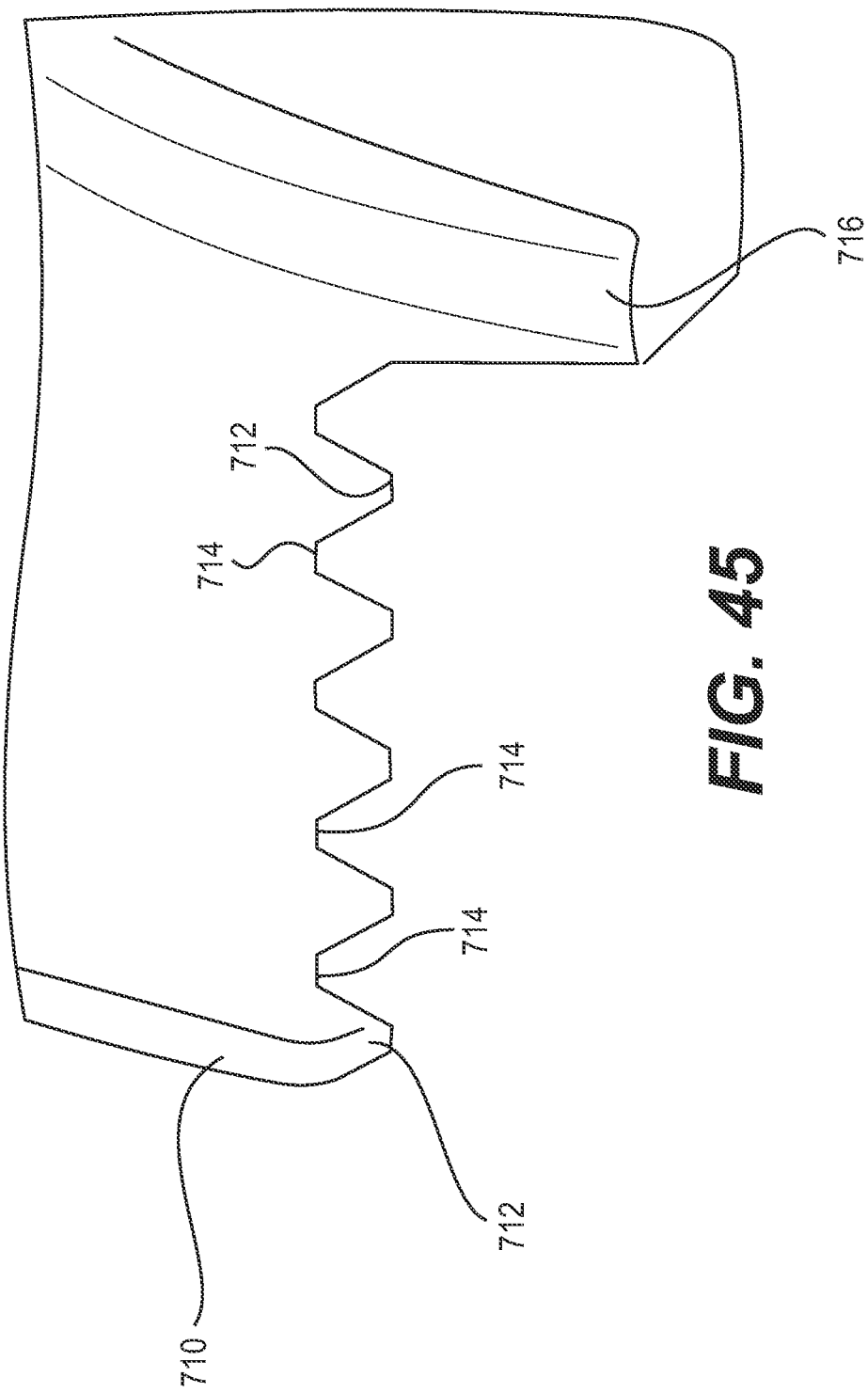
FIG. 45 is a side elevational view of a free end of the allograft lamina plate assembly shown in FIG. 43.

Additionally, as shown in FIG. 45, each of first free end 704 and second free end 706 includes a lower face 710 such that lower face 710 has a plurality of ridges 712 with adjacent grooves 714 formed therein. Further, an extension 716 extends anteriorly from lower face 710.

Ridges 712 and grooves 714 allow assembly 700 to be lagged into vertebra 50 as its securing screw 60 is inserted through foot 450 (or 450') to give additional fixation for assembly 700, promoting bony ongrowth to allow vertebra 50 to fuse with assembly 700. Also, the extension 716 allows the surgeon to size the appropriate sized assembly 700 to fit the particular patient, and to bump up against the lateral mass for optimum fixation of assembly 700.

Additionally, referring to FIG. 46, body 702 includes an outer face 720 having a plurality of laterally extending ridges 722 formed therein. Ridges 722 provide a rough surface to encourage tissue ongrowth. Also, posterior portion 708 includes a plurality of pilot holes 724 extending generally anteriorly therethrough. Pilot holes 724 are sized to allow bone pins (not shown) to be used to fix muscle thereto. Such additional fixation may aid in muscle reattachment to help reform the posterior tension band.

If femur segment 70 is too small, as shown FIG. 47 and/or if assembly 700 is required to be a larger size, an assembly 800 can be a body 802 constructed from multiple segments 804, 806, as shown in FIGS. 48 and 49. As shown in FIG. 49, segment 804 can include a male connection 808 that is inserted into a female connection 810 in segment 806.

Figure 51:
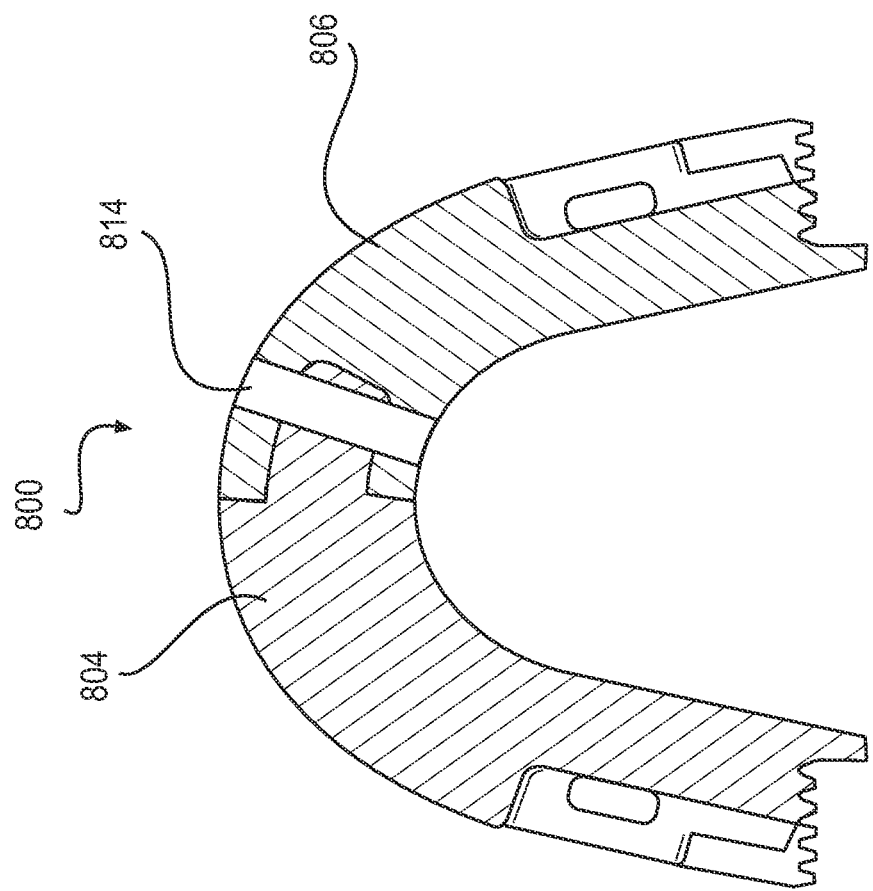
FIG. 51 is a third sectional view of the allograft lamina plate assembly shown in FIG. 48, showing a second securing pin.
Figure 50:
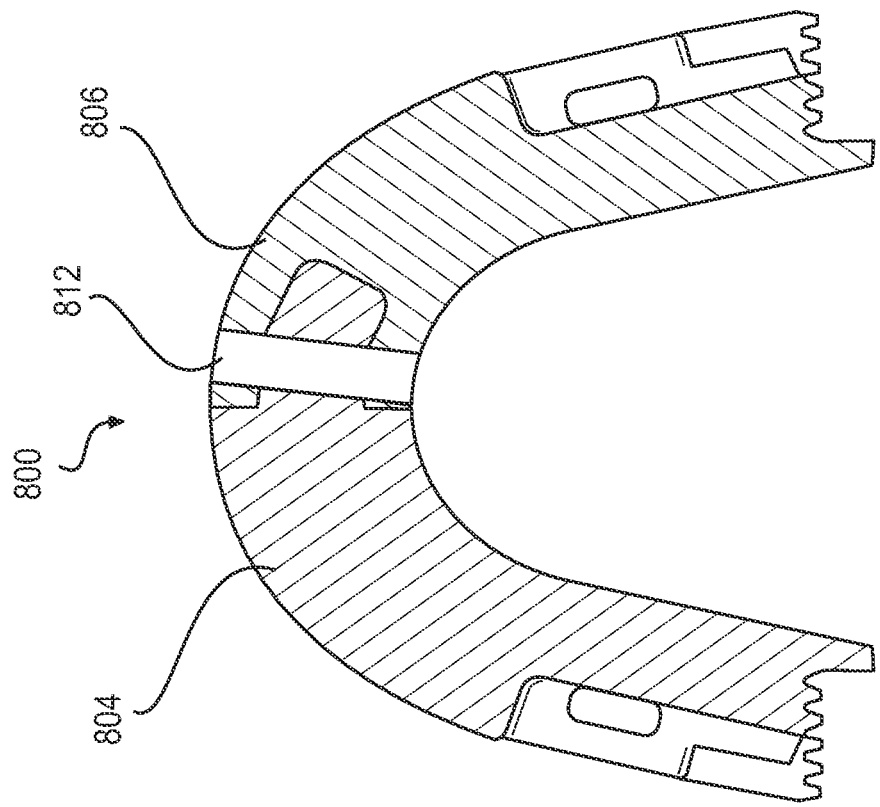
FIG. 50 is a second sectional view of the allograft lamina plate assembly shown in FIG. 48, showing a first securing pin.

As shown in FIGS. 48, 50, and 51, bone pins 812, 814 are inserted through both female connection 808 and female connection 810 to secure segment 804 and segment 806 to each other.

As shown in FIGS. 52 and 53, assembly 800 can incorporate the same connection for foot 450 (and foot 450') as discussed above with respect to assembly 700 (and assembly 400).

Alternatively, as shown in FIGS. 54 and 55, an alternative allograft assembly 900 ("assembly 900") is angled as compared to straight assemblies 700, 800. Assembly 900 allows for an angled insertion using an angled foot 920. Each free end 902 of assembly 900 includes pilot holes 904 that are sized to allow screws 60 to secure foot 920 to free end 902.

Figure 42:
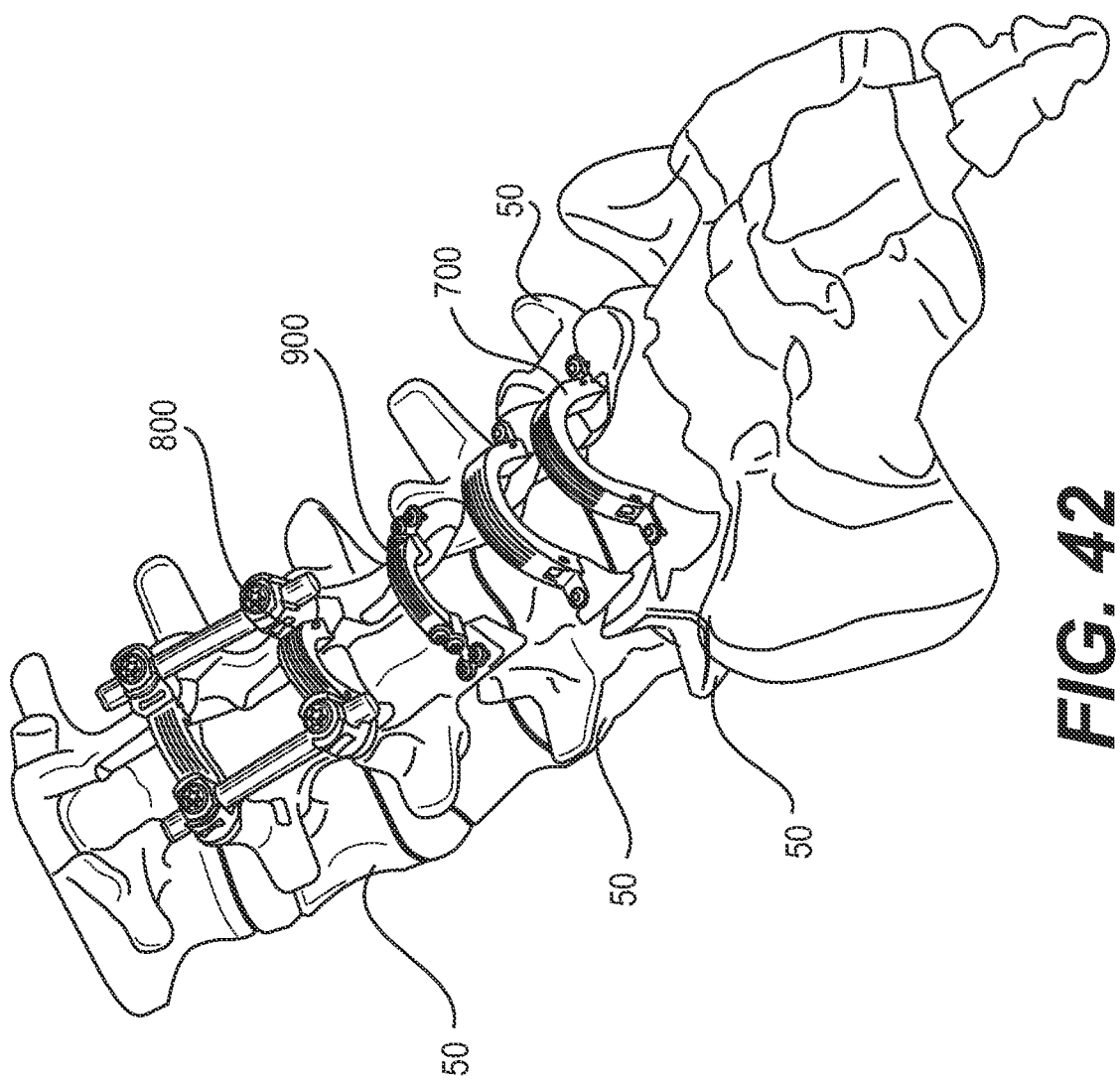
FIG. 42 is a perspective view of a plurality of alternative embodiments of allograft lamina plate assemblies attached to individual vertebrae along a spinal column.
Figure 43:
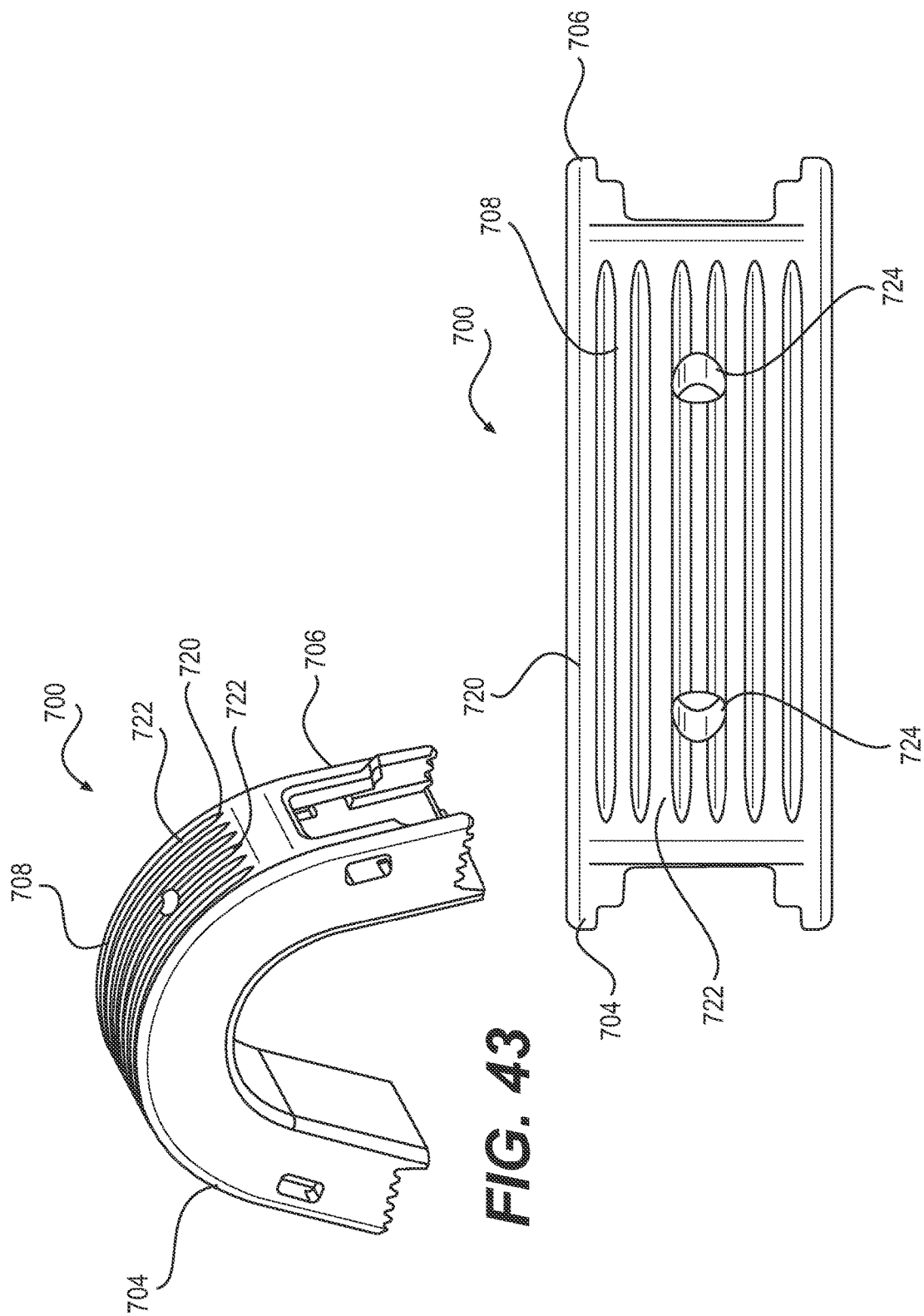
FIG. 43 is a perspective view of an allograft lamina plate assembly according to an exemplary embodiment.

Foot 920 has a first end 922 with openings 924 that are spaced to align with pilot holes 904, such that screws 60 can be inserted through openings 924 and into pilot holes 904. Foot 920 also has a second end 926 with openings 928 that allow foot 920 to be secured to vertebra 50, as shown in FIG. 42. Second end 926 extends along a plane and openings 924 in first end 922 extend along a line oblique to the plane, allowing for the angled alignment of assembly 900.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A lamina plate assembly comprising:
   an elongate body having:
      a first free end;
      a second free end; and
      a posterior portion disposed between the first free end and the second free end;
   a first foot adapted to be slidably coupled to the first free end; and
   a second foot adapted to be slidably coupled to the second free end;
   wherein each of the first foot and the second foot includes an opening formed therein sized to allow a bone fastener to extend therethrough and secure a corresponding one of the first foot and the second foot to the vertebral body;
   wherein each free end includes a locking slot;
   wherein each foot includes a wing adapted to flex inwardly and then extend outwardly into the locking slot.

2. The lamina plate of claim 1, wherein:
   each free end includes a recessed slot;
   each foot includes a central tab adapted to be slidably received in the corresponding recessed slot.

3. The lamina plate of claim 1, wherein the each foot includes a relief disposed inwardly of the wing.

4. The lamina plate of claim 3, wherein the relief includes a closed end and an open end opposite the closed end.

5. The lamina plate of claim 3, wherein the relief is a closed relief.

6. The lamina plate of claim 1, wherein the locking slot is a through opening accessible through a side wall of the free end for unlocking the wing from the locking slot.

7. The lamina plate of claim 1, wherein the posterior portion includes a first portion and a second portion pivotally coupled to the first portion.

8. The lamina plate of claim 7, wherein each of the first and second portions includes a plurality of graft windows and suture holes.

9. The lamina plate of claim 1, wherein the posterior portion includes a plurality of graft windows and suture holes.

10. A lamina plate assembly comprising:
an elongate body having:
a first free end having a recess;
a second free end having a recess; and
a posterior portion disposed between the first free end and the second free end;
a first foot adapted to be slidably coupled to the first free end through the first foot recess and fixed to one side of a vertebral body; and
a second foot adapted to be slidably coupled to the second free end through the second foot recess and fixed to the other side of the vertebral body;
wherein each of the first foot and the second foot includes an opening sized to allow a bone fastener to extend therethrough and secure a corresponding one of the first foot and the second foot to the vertebral body,
wherein the posterior portion includes a first portion and a second portion pivotally coupled to the first portion.

11. The lamina plate of claim 10, wherein each foot includes a central tab adapted to be slidably received in the corresponding recess.

12. The lamina plate of claim 10, wherein:
each free end includes a locking slot;
each foot includes a wing adapted to flex inwardly and then extend outwardly into the locking slot.

13. The lamina plate of claim 12, wherein the each foot includes a relief disposed inwardly of the wing.

14. The lamina plate of claim 13, wherein the relief includes a closed end and an open end opposite the closed end.

15. The lamina plate of claim 13, wherein the relief is a closed relief.

16. The lamina plate of claim 12, wherein the locking slot is a through opening accessible through a side wall of the free end for unlocking the wing from the locking slot.

17. The lamina plate of claim 10, wherein each of the first and second portions includes a plurality of graft windows and suture holes.

18. The lamina plate of claim 10, wherein the posterior portion includes a plurality of graft windows and suture holes.

* * * * *